(12) United States Patent
Garbe et al.

(10) Patent No.: US 8,329,865 B2
(45) Date of Patent: Dec. 11, 2012

(54) ANTIMICROBIALLY ACTIVE PEPTIDES

(75) Inventors: Claus Garbe, Tuebingen (DE); Birgit Schittek, Stuttgart (DE)

(73) Assignee: Eberhard-Karls-Univresitaet Tuebingen Universitaetsklinikum, Tuebingen (DE)

( * ) Notice: Subject to any disclaimer, the term of this patent is extended or adjusted under 35 U.S.C. 154(b) by 0 days.

(21) Appl. No.: 12/043,920

(22) Filed: Mar. 6, 2008

(65) Prior Publication Data

US 2009/0124546 A1 May 14, 2009

Related U.S. Application Data

(63) Continuation-in-part of application No. 10/735,481, filed on Dec. 12, 2003, now Pat. No. 7,348,409, which is a continuation of application No. PCT/EP02/06238, filed on Jun. 7, 2002.

(30) Foreign Application Priority Data

Jun. 13, 2001 (DE) .................................. 101 29 983

(51) Int. Cl.
*A61K 38/00* (2006.01)
*A61K 39/00* (2006.01)
*C07K 1/00* (2006.01)
*C07K 14/00* (2006.01)
*C07K 2/00* (2006.01)
*C07K 4/00* (2006.01)
*C07K 5/00* (2006.01)
*C07K 7/00* (2006.01)
*C07K 16/00* (2006.01)
*C07K 17/00* (2006.01)
*C12P 21/04* (2006.01)
*A01N 25/34* (2006.01)

(52) U.S. Cl. .... 530/350; 530/300; 435/69.7; 424/184.1; 424/404

(58) Field of Classification Search ........................ None
See application file for complete search history.

(56) References Cited

U.S. PATENT DOCUMENTS

| | | | | |
|---|---|---|---|---|
| 5,834,192 A * | 11/1998 | Akerblom et al. | ................ | 435/6 |
| 6,008,195 A | 12/1999 | Selsted | | |
| 6,420,116 B1 | 7/2002 | Olsen et al. | | |
| 7,718,618 B2 * | 5/2010 | Gallo et al. | ................ | 514/2.4 |
| 7,776,823 B2 * | 8/2010 | Gallo et al. | ................ | 514/2.4 |
| 2010/0273748 A1 * | 10/2010 | Gallo et al. | ................ | 514/167 |
| 2011/0207657 A1 * | 8/2011 | Eckert et al. | ................ | 514/2.6 |

FOREIGN PATENT DOCUMENTS

WO WO 99/64439 A2 12/1999
WO WO 2007/133730 A2 * 11/2007

OTHER PUBLICATIONS

Greenspan et al. (Nature Biotechnology 17: 936-937, 1999).*
Bowie et al. (Science, 1990, 257:1306-1310).*
Schittek et al., Nature Immunology, 2001; 2(12): 1133-37.*
Flad et al., Journal of Immunological Methods, 2002; 270: 53-62.*
Steffen et al., Antimicrobial Agents and Chemotherapy, 2006; 50(8): 2608-2620.*
Bowie et al. 1990 "Deciphering the Message in Protein Sequences: Tolerance to Amino Acid Substitutions" *Science* 247(4948):1306-1310.
Creighton, T.E. 1984 Proteins: Structures and Molecular Properties, pp. 314-315.
Creighton, T.E. 1989 Protein Structure: A Practical Approach, pp. 184-186.
Cunningham et al. 1998 "Identification of a survival-promoting peptide in medium conditioned by oxidatively stressed cell lines of nervous system origin." *Journal of Neuroscience* 18(18):7047-60.
Cunningham et al. 2000 "Calreticulin binding and other biological activities of survival peptide Y-P30 including effects of systemic treatment of rats" *Experimental Neurology* 163:457-468.
Hipfel et al. 2000 "Specifically regulated genes in malignant melanoma tissues identified by substractive hybridization" *Bristish Journal of Cancer* 82(6):1149-1157.
Nosoh, Y. et al. 1991 Protein Stability and Stabilization through Protein Engineering, Chapter 7, pp. 197.
Schittek et al. 2001 "Dermcidin: a novel human antibiotic peptide secreted by sweat glands" *Nature Immunology* 2(12):1133-1137.
Schroeder, J.M. 1999 "Epithelial peptide antibiotics" *Biochem Pharmacol* 57:121-134.
UniProtKB/Swiss-Prot entry P81605 http://ca.expasy.org/uniprot/P81605 pp. 1-4.

* cited by examiner

*Primary Examiner* — Vanessa L Ford
*Assistant Examiner* — Lakia Tongue
(74) *Attorney, Agent, or Firm* — Knobbe Martens Olson & Bear LLP

(57) ABSTRACT

An antimicrobially active peptide comprises the DCD protein or a fragment of DCD, preferably derived from the C-terminal region.

6 Claims, 13 Drawing Sheets

Fig 1A

5'-UTS →
5'-GACCCTAGAT CCCAAGATCT CCAAGGATTT GGTGGCATAC CCACTCCAGC ACACAGAAGC ATGAGGTTCA
                                                                    start codon exon 1                              intron 1           exon 2
TGACTCTCCT CTTCCTGACA GCTCTGGGCAG GAGCCCTGGT CTGTGCCT ⇑ AT GATCCAGAGG CCGCCTCTGC intron 2         exon 3
CCCAGGATCG GGGAACC ⇑ CTT GCCATGAAGC ATCAGCAGCT CAAAAGGAAA ATGCAGGTGA AGACCCAGGG intron 3           exon 4
TTAGCCAGAC AGGCACCAAA GCCAAGGAAG CAGAGATCCA GCCCTCTGG ⇑ A AAAAGGCCTA GACGGAGCAA intron 4
AAAAAGCTGT GGGGGGACTC GGAAAACTAG GAAAAGATGC AGTCGAAGAT CTAGAAAGCC TGGGTAAAGG ⇑ exon 5                                      stop codon
AGCCGTCCAT GACGTTAAAG ACGTCCTTGA CTCAGTACTA TAGCTGTAAG GAGAAGCTGA GAAATGATAC
                                            ← 3'-UTS
CCAGGAGCAG CAGGCTTTAC GTTTTCAGCC TAAAACCT

Fig 1B

MRFMTLLFLT ALAGALVCAY DPEAASAPGS GNPCHEASAA QKENAGEDPG LARQAPKPRK QRSSLLEKGL
DGAKKAVGGL GKLGKDAVED LESVGKGAVH DVKDVLDSVL

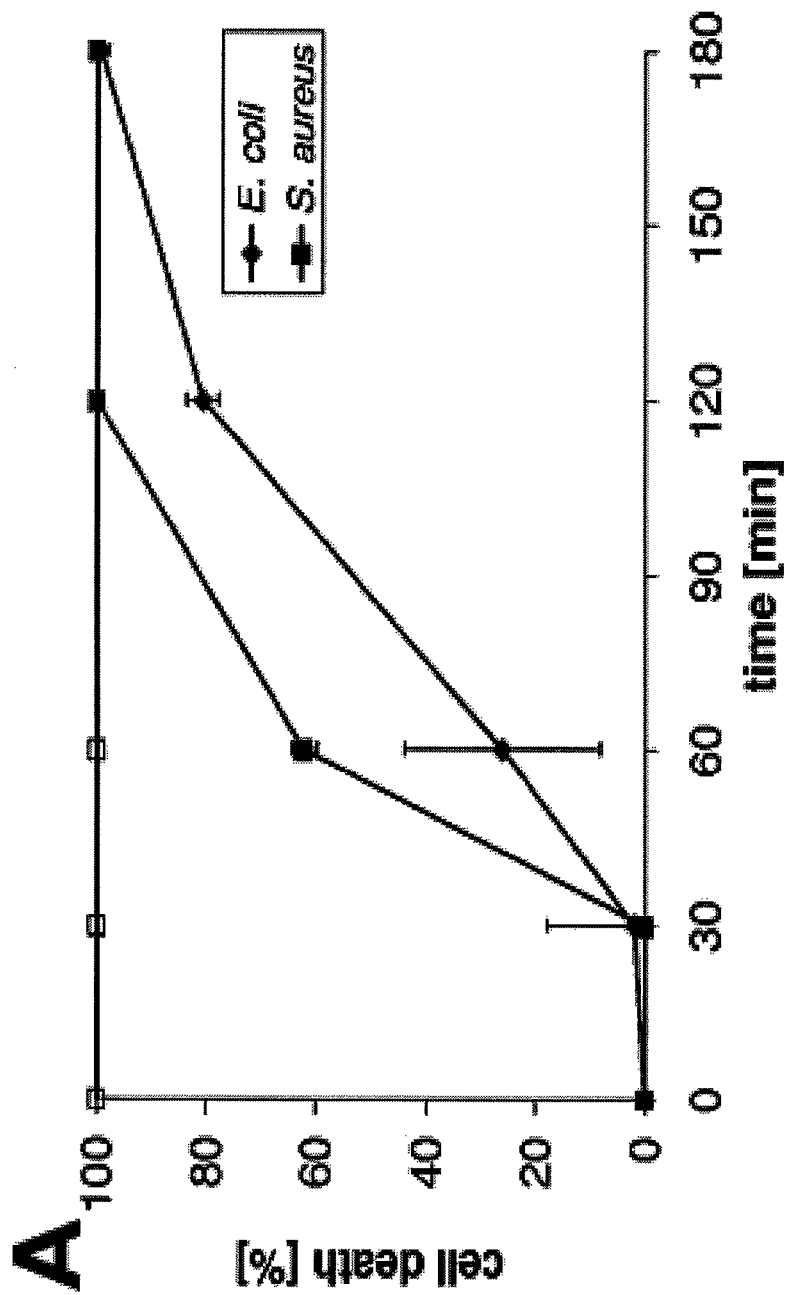

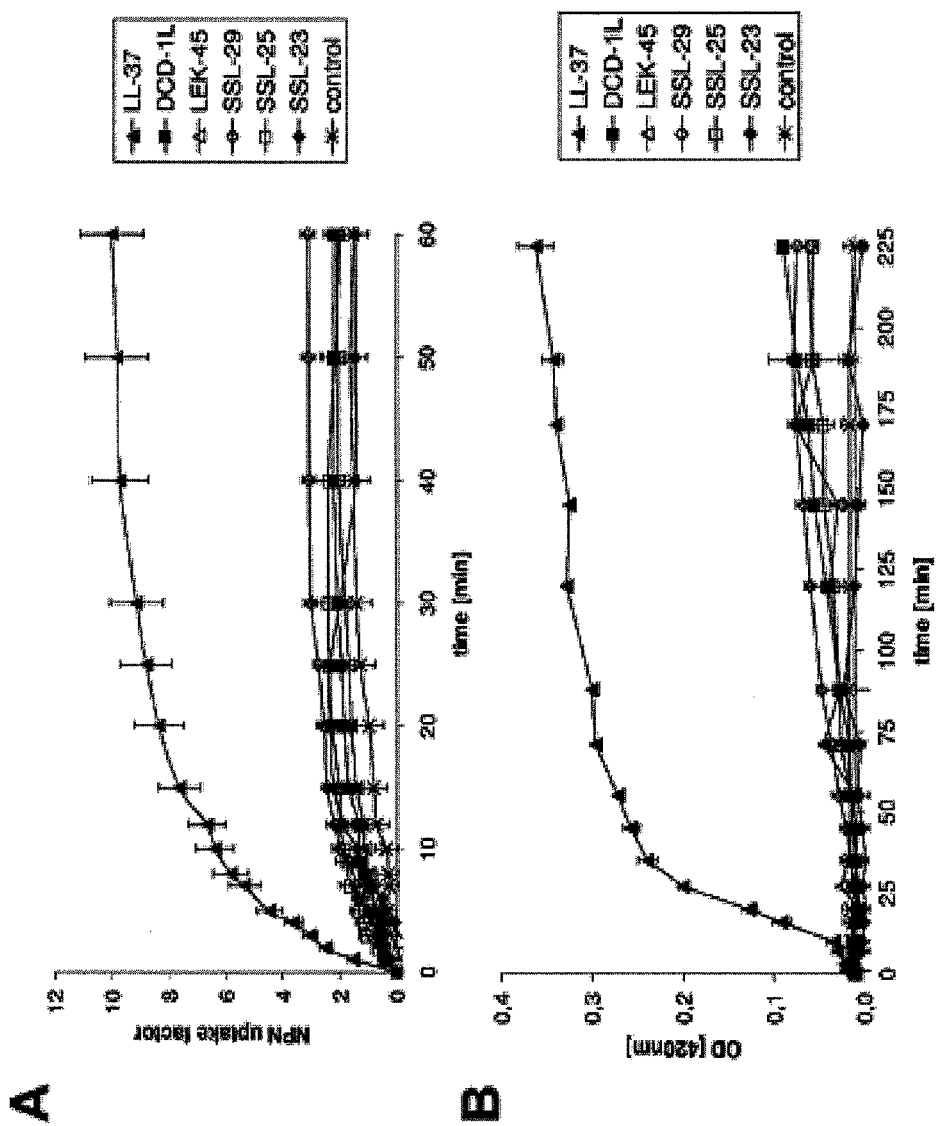
Fig. 9A and B

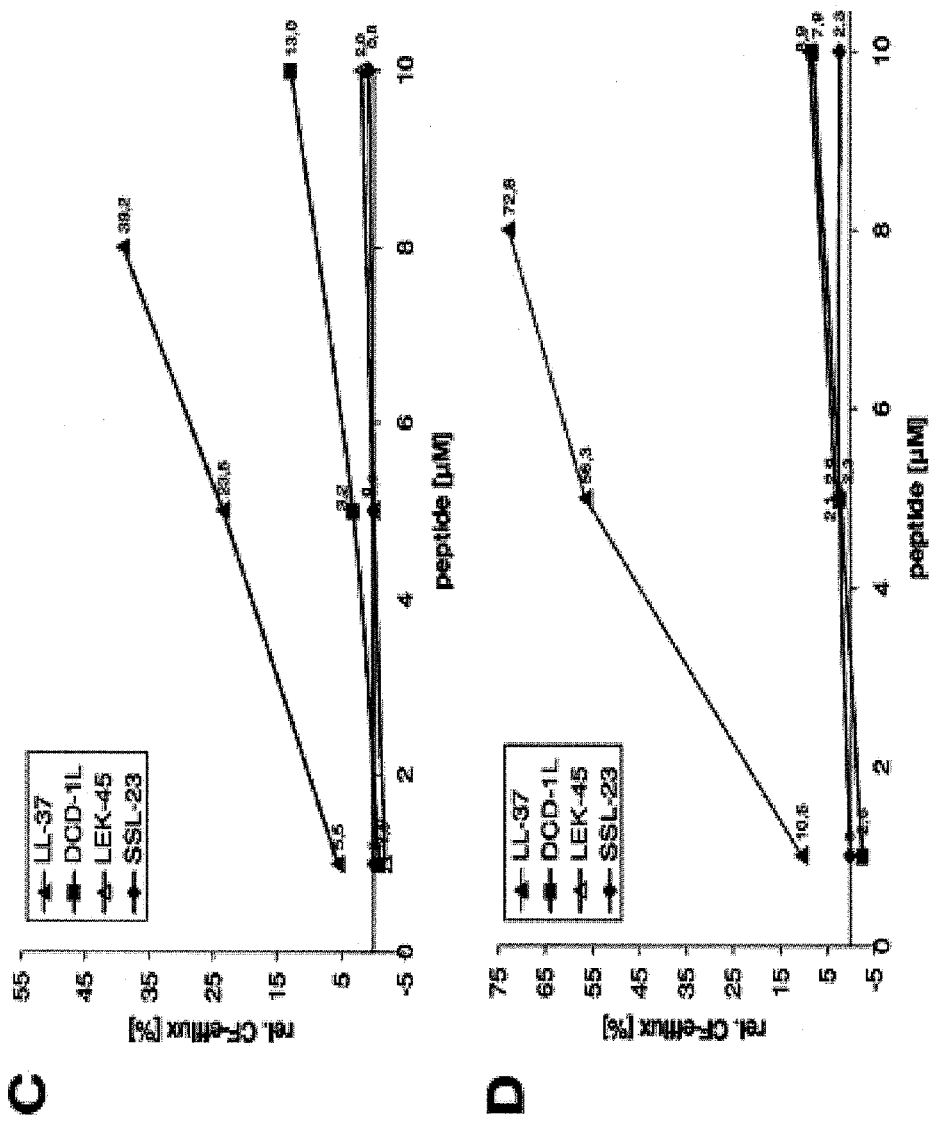
Fig. 9C and D

ANTIMICROBIALLY ACTIVE PEPTIDES

CROSS-REFERENCES TO RELATED APPLICATIONS

This application is a continuation-in-part of U.S. application Ser. No. 10/735,481, filed Dec. 12, 2003, which is a continuation of international patent application PCT/EP02/06238 filed 7 Jun. 2002, designating the U.S., which claims priority of German patent application DE 101 29 983.4 filed on Jun. 13, 2001, all of which are incorporated herein by reference in their entireties.

BACKGROUND OF THE INVENTION

1. Field of the Invention

The present invention relates to an antimicrobially active peptide and to its preparation and to a method for protecting and/or treating human skin against microorganisms.

2. Description of the Related Art

The epithelial tissue of mammals represents an important barrier to the surroundings and provides a first line of defense against invading microorganisms. In particular, antimicrobial peptides, of which there are many in the epidermis, participate in the defense system. They control microbial growth in the first hours after epithelial injury and during wound healing. In particular, they can be found in some inflammatory disorders of the skin.

To date, two classes of antimicrobial peptides have been discovered in mammalian skin, the cathelicidins and the β-defensins. They are induced in human creatinocytes after induction by inflammatory stimuli and act primarily as a response to injuries and not within the framework of a constant modulation of the epithelial defense mechanism.

Whereas, for example, cathelicidin PR-39 is a component of wound fluid and appears to be involved in wound healing, cathelicidin LL-37 is expressed in human skin creatinocytes at inflammatory sites in various diseases.

Defensins are small cationic peptides having a molecular weight of from 3 to 5 kDa, and they have an antibacterial and antimycotic effect. The α-defensins HD1-4 are expressed for example in human neutrophils which accumulate in infected tissue regions. The α-defensins HD-5 and HD-6 are, by contrast, produced by epithelial granulocytes.

In general, antimicrobial peptides are endogenous, gene-encoded peptides with particular importance for the early phase of defense against microbial pathogens. They can be detected within minutes to hours after the first contact with the pathogen.

However, known antimicrobial peptides do not act against all microbial pathogens in the same way; for example defensins have only an inadequate effect on infections with *S. aureus*, an important cause of skin infections, especially associated with atopic dermatitis.

Antibiotics are also employed preventively or curatively for controlling pathogenic microorganisms, these being substances of microbiological origin which inhibit the growth of or even kill other microorganisms. In contrast to the abovementioned cathelicidins and defensins, antibiotics usually have selective activity. Many microorganisms have a natural insensitivity to an antibiotic, but they may also develop this so-called antibiotic resistance during growth in the presence of antibiotics.

Mutation and selection processes, and the development of resistances are causing problems increasingly frequently, not only in clinical routine but also in the manufacture of medicaments and cosmetics, with microbial pathogens which can be controlled inefficiently or not at all.

Against this background, there is a continuing need for novel antimicrobially active agents which can be employed preventively or curatively.

Against this background, an object underlying the present invention is to provide a further antimicrobially active peptide and indicate a way for producing it.

SUMMARY OF THE INVENTION

This object is achieved according to the invention by an anti-microbially active peptide which comprises the DCD protein comprising the sequence SEQ ID No: 1 from the appended sequence listing, or a DCD fragment preferably derived from the C-terminal region.

This object underlying the invention is completely achieved in this way.

This is because the inventors of the present application have been able to identify, in a skin cDNA library, a gene which they have called dermcidin (hereinafter: DCD). The gene consists of five exons and four introns and is located on chromosome 12q13 between the D12S1896 and D12S1632 markers (lod score 14.11).

DCD has a very restrictive expression pattern because the gene is expressed only in human skin and was undetectable neither in 50 analyzed human tissues of various origins nor in human fibroblasts, keratinocytes, melanocytes or melanoma cell lines.

The gene encodes a peptide which belongs to a new class of antimicrobial proteins and displays broad-spectrum activity. The peptide is specifically expressed in sweat glands, secreted in the sweat and transported to the epidermal surface. In sweat, it is proteolytically processed to a peptide which displays a dose-dependent antimicrobial effect on a large number of pathogenic microorganisms. The inventors have been able to show, using an antimicrobial assay, that the DCD protein is toxic for *Escherichia coli, Enterococcus faecalis, Staphylococcus aureus* and *Candida albicans*.

Until the present invention, no antimicrobial peptides had been discovered in human sweat. From the finding of DCD, and from the experimental demonstration that DCD and fragments of DCD have antimicrobial effects, the inventors of the present application conclude that sweat plays a role in regulation of the human skin flora and that DCD has therapeutic importance for the treatment of disorders of the skin. The amount of DCD present in sweat is 1-10 µg/ml, and exactly this concentration range exhibits an antimicrobial effect on the abovementioned pathogens in the experimental approach.

Comparison with GenBank surprisingly revealed that the cDNA sequence of DCD has been published by Akerblom et al. as "human cachexia associated protein" (HCAP). The authors describe in U.S. Pat. No. 5,834,192 the identification and isolation of HCAP from a breast tumor library and propose the therapeutic use of HCAP and of the encoding gene within the framework of treatment of tumor-induced cachexia. An antimicrobial effect of HCAP is not disclosed.

It is of interest that a short segment in the N-terminal region of DCD—amino acid residues 20-49—shows 96 percent homology with a "survival promoting peptide" called Y-P30; see Cunningham et al.: "Calreticulin Binding and Other Biological Activities of Survival Peptide Y-P30 Including Effects of Systemic Treatment of Rats", *Experimental Neurology* 163:254-268 (2000).

Y-P30 was purified from oxidatively stressed neural cell lines and apparently has a survival-favoring effect on neurons, because direct application of this peptide to lesions of the rat cerebral cortex permits the survival of neurons which normally degenerate after a cortical lesion. The authors propose that Y-P30 is secreted by neural cells for the purpose of cytoprotection as a response to stress.

It is preferred, in a further development of the invention, for the fragment to comprise a maximum of 50 amino acid residues from the C-terminal region of DCD, preferably either the amino acid residues 63-110 (SEQ ID No: 2) or amino acid residues 63-109 (SEQ ID No: 3).

It has emerged that these fragments have an outstanding antimicrobial effect, in particular on the abovementioned pathogens. Since these fragments are also distinctly shorter than the mature DCD protein, which comprises 110 amino acid residues, with the first 19 N-terminal amino acid residues being a signal peptide, they can be prepared more easily and less expensively both by chemical synthesis and biotechnologically than the mature DCD protein. However, the smaller size of the fragments compared with the mature DCD protein also has, besides the possibility of easier and less expensive preparation, the further advantage that shorter fragments are ordinarily more stable than longer ones, so that both manipulation and administration of the fragments is simpler than with the mature protein and thus displays further advantages.

Also a further truncation of the two fragments SEQ ID No: 2 and SEQ ID No: 3 at the N-terminal end impair the antimicrobial effect, whereas the inventors have been able to establish that a truncation to the 31 C-terminal amino acid residues of DCD leads to a peptide which has no appreciable antimicrobial effect.

It is further preferred, compared with the corresponding position in the mature DCD protein, for at least one amino acid to be exchanged for an amino acid of the same group.

It is known that the so-called proteinogenic amino acids can be divided into four groups, and that replacement of one amino acid in a peptide by an amino acid of the same group frequently alters the function of the peptide only slightly or not at all. Such an amino acid exchange may be worthwhile in particular in relation to a chemical synthesis or a biotechnological production if the corresponding peptide can, by reason of the exchange, be produced in a higher yield, the antimicrobial effect being retained owing to the exchange within one group.

It may be mentioned, only for the sake of completeness, that the amino acid groups are characterized as follows: I. amino acids with neutral and hydrophobic (nonpolar) side chains, II. amino acids with neutral and hydrophilic (polar) side chains, III. amino acids with acidic and hydrophilic (polar) side chains and IV. amino acids with basic and hydrophilic (polar) side chains.

A further object of the invention is a peptide which comprises an amino acid sequence homologous to the novel peptide and shows a comparable antimicrobial effect.

A homologous peptide means within the scope of the present invention a peptide which has arisen by divergent evolution from a common precursor of DCD and displays great correspondence not only in the primary structure but also in the secondary structure and tertiary structure, is produced in a biologically comparable way, and has a comparable function. This is because, as the inventors have been able to show that DCD protein which is expressed in human sweat glands and is secreted and processed, and C-terminal fragments of the DCD protein, respectively, some of which occur naturally in human sweat, display an antimicrobial effect, it is possible to find corresponding homologous peptides in other mammals without difficulty. Starting from the surprising finding that at least one antibacterially active peptide is present in human sweat, the steps for finding homologous peptides also in other mammals are prefigured to such an extent that they are included in the present invention.

In a further development, it is preferred for the peptide to have at least one post-translational modification.

Post-translational modification means within the scope of the present application in particular the attachment of prosthetic groups (for example glycosylation) and modification of amino acid residues (for example alkylation). Thus, in the general sense, a post-translational modification means any difference between the functional peptide employed according to the invention and the linear sequence of the unmodified amino acid residues.

Such post-translational modifications may serve the stability of the peptide or an increased biological activity, but may also be attributable to a biotechnological production. Thus, production of peptides in prokaryotic cells leads to a reduced form of the peptide, whereas production in eukaryotic cells may lead to a glycosylated peptide. It may additionally be worthwhile to provide at least one of the amino acids of the peptide with a protective group in order to protect the peptide from attack by exopeptidases.

It is preferred in one embodiment for the peptide to be connected to a further peptide or protein to give a fusion protein, in which case the further peptide or protein is preferably selected from the group: signal peptide, reporter protein, histidine tags, antigenic determinants etc.

If peptides are synthesized as fusion peptides, the preparation and purification of the peptides according to the invention may be facilitated. In this case, sequences encoding amino acid segments or domains of known proteins are fused onto nucleic acids encoding the peptides of the invention, so that a continuous peptide is generated on expression. Examples of such fused-on amino acid segments are, for example, the histidine tags, by means of which the expressed fusion proteins can be purified on nickel chelate acids, or antigenic determinants, which permit the peptides to be purified on suitable antibody affinity columns. Signal peptides may ensure reliable exportation of the generated peptide, while reporter proteins, such as, for example, eGFP (enhanced green fluorescent protein) makes optical detection of the generated peptide possible.

As already mentioned, the novel peptide can be prepared by chemical synthesis, also called Merrifield synthesis, or by techniques of molecular biology.

Against this background, a further object of the invention is a nucleic acid molecule comprising a sequence segment encoding a peptide according to the invention, to an expression vector comprising such a nucleic acid molecule and, where appropriate, control sequences, in particular for replication, transcription and/or translation, and to a host cell which is transfected or transformed with the expression vector.

Since the amino acid sequence of the peptide of the invention is known, a corresponding nucleic acid sequence can be deduced with the aid of the genetic code, it being possible to use optimized codons for different hosts (bacteria, yeast, mammalian cells). However, the codon choice evident from FIG. 1 is preferred.

Preparation of a peptide according to the invention by nucleic acid expression has the advantage that the peptide can be prepared in virtually unlimited quantities. However, the peptide can also in addition be modified in a simple manner by, specifically, modifying the corresponding coding sequence at the nucleic acid level in order thus to bring about an amino acid exchange. At the nucleic acid level it is also possible to produce probes in order to search for homologous peptides in sweat glands of other mammalian cells.

As already mentioned, a further object of the invention is a method for protecting and/or treating human skin against microorganisms, comprising the step of administering a peptide according to the invention onto human skin.

Since DCD is expressed in sweat glands, the inventors have realized that the peptides according to the invention are particularly suitable for the protection and treatment in particular of human skin.

Against this background, another object of the invention is a pharmaceutical or cosmetic composition which comprises as active ingredient a peptide of the invention in an antimicrobially effective amount, preferably in the region of 1-50 µg/ml.

It will be appreciated that the features mentioned above and yet to be explained hereinafter can be used not only in the combinations indicated in each case but also in other combinations or alone without leaving the scope of the present invention.

BRIEF DESCRIPTION OF THE DRAWINGS

Further advantages are evident from the following description in connection with the drawings. These show:

FIG. 1 in FIG. 1A the DNA sequence for DCD (SEQ ID NO: 6) and in FIG. 1B the amino acid sequence (SEQ ID NO: 1);

FIG. 9. Effect of DCD-derived peptides on membrane permeability. (A) Outer membrane permeability measured by peptide-mediated NPN uptake in E. coli ML-35p. E. coli cells were incubated with 10 µM NPN in the presence of various concentrations of DCD peptides in 5 mM sodium HEPES buffer (pH 7.4). Enhanced uptake due to membrane permeability was measured by an increase in fluorescence intensity (Ex350 and Em460) caused by partition of NPN into the hydrophobic interior of the outer membrane. At time point 0 min, intact E. coli ML-35p cells were added to the peptides. The results are expressed as NPN uptake factor of fluorescence in arbitrary units. All analyses were performed in triplicates. (B) Inner membrane permeability measured as the influx of ONPG in E. coli ML-35p after the addition of DCD peptides. Stationary-growth-phase E. coli were incubated for 3 h at room temperature in 10 mM NaP (pH 7.0) with 1.67 mM ONPG. The release of ONP by cytoplasmic β-galactosidase was spectrophotometrically monitored at 420 nm. In the reference cuvette, peptides were placed in solvent. All samples were analyzed in triplicates. (C and D) Influence of the peptides DCD-1L (■), LEK-45 (Δ), and SSL-23 (♦) on CF efflux of unilamellar liposomes made of DOPC (C) and DOPC-DOPG (1:1 molar ratio) (D). Release was determined 4 min after peptide addition at concentrations of 1 to 10 µM. At 4 min the amount of leakage reached a plateau when liposomes still contained a significant amount of CF. Reaction progress was expressed as the percentage of CF released relative to the total fluorescence released after the addition of Triton X-100 solution at the end of each experiment.

DETAILED DESCRIPTION OF THE PREFERRED EMBODIMENT

Example 1

Figure 2:
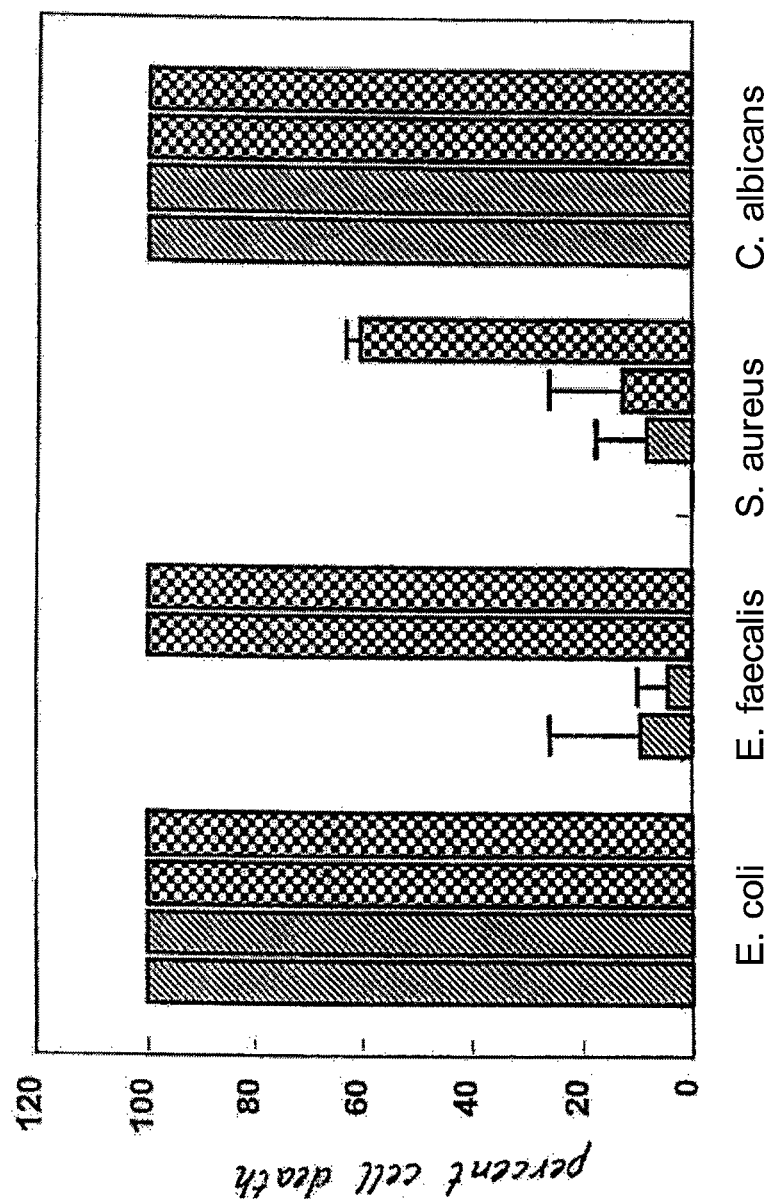
FIG. 2 in a bar diagram the quantity-dependent antimicrobial effect of the DCD-eGFP fusion protein on various microbial pathogens with an incubation time of 4 h.

Isolation of the DCD cDNA and Determination of the Genomic Sequence

In the screening of a subtractive cDNA library of primary melanoma tissue and benign melanocyte nevus tissue using cDNA arrays, a clone which was over expressed in the nevus tissue compared with the melanoma tissue and which, at the time of isolation, had no sequence homology with a gene published in GenBank was isolated; Hipfel et al., "Specifically Regulated Genes in Malignant Melanoma Tissues Identified by Subtractive Hybridization", British Journal of Cancer 82, 1149-1157 (2000). The clone referred to as clone 8 in the publication therein was subsequently called dermcidin (DCD).

The full length of the DCD cDNA was determined by sequencing overlapping PCR products, and it is 458 bp with an open reading frame of 330 bp, which codes for 110 amino acid residues. The gene consists of five exons and four introns and is expressed as a single transcript.

FIG. 1A indicates the genomic sequence of the DCD gene for the five exons, and FIG. 1B shows the peptide sequence which is to be found as SEQ ID No: 1 in the sequence listing. The first 19 N-terminal amino acid residues of the 110 amino acid residues represent a signal peptide.

DCD was assigned to chromosome 12q13 between the D12S1896 and D12S1632 markers (lod score 14.11). The molecular weight of the unmodified protein is 11.2 kDa including the signal peptide and 9.5 kDa without the signal peptide.

Example 2

Detection of DCD in Various Tissue Samples

The DCD expression profile was determined by testing by the dot-blot technique RNA from fifty different tissues and development stages, using labeled DCD cDNA as probe. No detectable signal was found in any of the fifty samples.

In order to analyze whether the DCD gene is expressed to only a very small extent in human tissue or human cell lines, an RT-PCR was carried out for the DCD gene (Clontech MTC Panels). It emerged that DCD is strongly expressed in human skin, human melanocytic nevus tissue and melanoma tissue, but that DCD is not expressed in the other sixteen human tissues analyzed or in fetal and various tumor tissues. In addition, no amplification products were found after an RT-PCR with forty cycles in different parts of the human digestive system and in various tumor cell lines either.

It can be inferred from these results that DCD expression is confined to cells in the skin.

The cell type which expresses the DCD gene was determined by means of in situ hybridization, immunohistochemistry, immunofluorescence and immunoelectron microscopy.

The in situ hybridization revealed that the gene is expressed in eccrine sweat glands within the dermis of the human skin. No signals were detected on use of a sense probe for DCD as negative control.

A DCD antiserum was raised in rabbits for the immunohistology, using as antigenic determinant the peptide KENAGEDPGLARQAPKPRKQRSSL (SEQ ID NO: 7) which was coupled to KLH for T-cell stimulation. The antigenic determinant corresponds to the amino acid sequence 42-65 from the DCD peptide. It emerged from the investigated skin sections that there was intense staining of the eccrine sweat glands, but no expression on other skin cell types.

For the immunofluorescence, the sections were stained with the polyclonal anti-DCD antiserum mentioned in the previous paragraph, and then incubated with an donkey anti-rabbit antibody labeled with Cy5 (Dianova, Hamburg). The myoepithelial cells of the secreting section of the eccrine sweat glands were then labeled with a monoclonal anti-actin antibody (Enzo Diagnostics, marketed by Loxo, Dossenheim, Germany), stained with a Cy3-labeled donkey anti-mouse antibody (Dianova, Hamburg) and all nuclei were stained with YOPRO (Molecular Probes, Leiden, the Netherlands). The sections were analyzed using a confocal laser scanning microscope (Leica TCS SP, Leica Microsystems, Benzheim) with 250× magnification.

A strong immunofluorescence staining was observable in the secreting sections of the eccrine sweat glands. Only a weak and greatly reduced staining was observable in secreting sections of apocrine sweat glands.

Finally, it was possible by immunoelectron microscopy to localize the DCD protein in the dark mucus-secreting cells of the secreting section of eccrine sweat glands. Ultrastructurally DCD was localized within the Golgi apparatus and in the secreting granules.

In a Western blot analysis of human sweat, three major protein bands were detected at approximately 17, 20 and 24 kDa using the abovementioned antiserum (amino acid residues 42-65 of DCD). The protein with the higher molecular weight was detected only in some sweat samples, whereas the other two bands are detected even when sweat is analyzed under non-reducing conditions.

It is evident from these data that full-length DCD is expressed in the dark mucus-secreting cells in sweat glands and is transported from the Golgi apparatus via secreting granules to the luminal surface of the cells, where the protein is secreted into the duct. It was possible to calculate from the Western blot analysis that the quantity of full-length DCD protein in sweat is between 1 and 10 µg/ml. The three major protein bands detected in the sweat and reacting with the DCD antiserum appear to be forms with different post-translational modifications of the complete DCD protein.

Example 3

Construction, Expression and Characterization of a DCD-eGFP Fusion Protein

The complete DCD cDNA without stop codon was cloned in frame into the pEGFP vector (Clontech, Heidelberg) 5' to the eGFP gene, thus generating a fusion gene called DCD-eGFP. The correct sequence was confirmed by sequence analysis.

SKMEL28 melanoma cells (PNAS 73, 3278-3282 (1976)) were transfected with 1-2 µg of DCD-eGFP or eGFP alone using Fugen (Roche, Mannheim) and cultivated in RPMI with 10% FCS.

After 48 hours, 500 µm/ml G418 (Calbiochem, Schwalbach) were added to the medium, and the amount of G418 was changed to 1 mg/ml after one week. The cells were kept in selection medium and cloned by limiting dilution. A stable clone from each transfection was used for further analysis. Cell lysates of the two clones ($5-7 \times 10^6$ cells) were prepared by incubating the cells in 1.2 ml of lysis buffer (PBS with 0.5% Triton X-100, 5 mM EDTA, 0.1 mM PMSF, 10 µM pepstatin A, 10 µM leupeptin, 25 µg/ml aprotinin) for 30 minutes. The lysates were separated from the nuclei by centrifugation at 12 000 rpm for 20 min. The supernatants, free of FCS, G418 and penicillin/streptomycin, of transfected and untransfected SKMEL28 control cells were concentrated and desalted by ultrafiltration using an Amicon filtration cell (10,000 Da) and Amicon Centricon Plus-20 columns with a Biomax-5 membrane (5,000 Da).

Western blot with the antiserum described in example 2 revealed in the cell lysate a fusion protein of 44 kDa and in the concentrated supernatant two proteins of 33 and 44 kDa. The eGFP protein (24 kDa) was found only in the cell lysate and not in the supernatant.

The amino acid composition of DCD was investigated further by incubating the concentrated supernatants with various proteases (Sigma, Taufkirchen) and loading the proteins onto an 11% SDS gel. Western blots were then carried out with an anti-GFP antibody.

The proteases trypsin (300 µg/ml) and chymotrypsin (300 µg/ml) were incubated in 10 mM Tris-HCL, pH 8.0, containing 2 mM $CaCl_2$ at 37° C. for 1 h. Two µl of ArgC endoproteinase (100 µg/ml) were incubated in a buffer which contained 0.1 M Tris-HCl pH 8.0, 8 mM $CaCl_2$, 50 mM DDT and 5 mM EDTA at 34° C. for 2 h.

The protease digestion of the fusion protein showed that DCD-eGFP is degraded to the size of the GFP protein by the proteases trypsin and chymotrypsin. The ArgC endoprotease, which cuts at the C-terminal end of arginine residues, was unable to degrade the fusion protein, although three potential cleavage sites are present in the full-length mature protein (without signal peptide); see FIG. 1b, where an arginine residue (R) is evident in positions 53, 59 and 62 of the mature protein.

It is evident from these results that the cleavage site for ArgC is not present in the fusion protein. Since, moreover, the fusion protein cannot be recognized by the DCD antiserum from example 2 in the Western blot, it is evident that DCD is processed proteolytically in order to yield a truncated peptide which lacks at least the first 47 amino acid residues of the secreted mature protein.

In other words, a peptide containing the last 48 C-terminal amino acid residues (62-110) or less is generated from the full-length DCD protein in sweat. This peptide lacks part of the antigenic determinant used for the immunization, and it is therefore undetectable by the antiserum from example 2. Although eccrine sweat glands can be stained with the antiserum, a stable DCD protein having the antigenic region was to be found only in some sweat samples. The DCD-eGFP fusion protein was also undetectable with the antiserum in the concentrated supernatant.

Example 4

Antimicrobial Tests

In order to elucidate the property of DCD and of the truncated DCD peptides further, inter alia the antimicrobial effect of the DCD-eGFP fusion protein, of a synthetically prepared peptide having the 48 C—terminal amino acid residues of DCD (SEQ ID No: 2) and of a peptide (SEQ ID No: 3) derived from HPLC fractionation of human sweat, was investigated. This latter peptide had a mass of 4702 daltons and corresponds to the sequence SEQ ID No: 2 apart from the C-terminal leucine. This peptide isolated from sweat is listed as SEQ ID No: 3 in the sequence listing.

The antimicrobial effect of said peptides was carried out by a CFU test (test for colony-forming units) as described for the defensins by Valore et al., "Human Beta-Defensin-1: An Antimicrobial Peptide of Urogenital Tissues", J Clin Invest 101, 1633-1642 (1998).

The test of the novel peptides was carried out with *Escherichia coli, Staphylococcus aureus, Enterococcus faecalis* and *Candida albicans*. *E. coli* was incubated in LB medium, *E. faecalis* and *S. aureus* in Columbia medium (Difko, BD Heidelberg) and *C. albicans* in casein hydrolysate medium (Merck, Darmstadt). The amounts of bacteria and yeasts were determined by photometry. The bacterial strains were incubated to an optical density of 0.7-0.4 at 600 nm and the yeast was incubated to an optical density of 0.4-0.6 at 450 nm. The amount of the organisms was determined by plating various dilutions as follows: an OD of 1 at 600 nm is equivalent to $8.2 \times 10^9$/ml for *E. coli*, $1.9 \times 10^{10}$/ml for *S. aureus* and $9.0 \times 10^9$/ml for *E. faecalis*, and an OD of 1 at 459 nm is equivalent to $1.4 \times 10^8$/ml for *C. albicans*.

The cells were washed twice with 10 mM sodium phosphate buffer (pH 7.4) and diluted to $2\text{-}3 \times 10^7$ cells/ml (*E. coli, E. faecalis*), $5.7 \times 10^7$ cells/ml (*S. aureus*) or $5 \times 10^5$ cells/ml (*C. albicans*) in phosphate buffer.

The cells were incubated with various amounts of the peptides in 200 µl of sodium phosphate buffer at 37° C. for 3 h, 4 h or overnight (21-24 h). The cells were diluted 1:10 to 1:100 for the bacteria and 1:500 to 1:5000 for the yeast, and 50 µl, 100 µl and 200 µl were plated on appropriate agar plates. The plates were incubated at 37° C. overnight, and the number of colonies was counted. The antimicrobial effect of the peptides has been stated as percentage of killed cells: [1−(cell survival after incubation with the peptide)/(cell survival after control incubation)]×100.

In addition to the fusion protein and the peptides of SEQ ID No: 2 and SEQ ID No: 3, the antimicrobial effect of eGFP, Y-P30 (YDPEAASAPGSGNPCHEASAAQKENAGEDP (SEQ ID NO: 4), this corresponds to the Y-P30 mentioned in the description, but with the amino acid K replacing C in position 23 in order to obtain 100% homology to the amino acid segment 19-39 of DCD), and a control peptide DPI (DPYAEAASGPNPGSKSHESAQAENCGADPE, (SEQ ID NO: 5)) was tested.

Whereas no appreciable antimicrobial effect was detectable for eGFP, Y-P30 and DPI, a quantity-dependent antimicrobial effect was shown by the DCD-eGFP fusion protein and by the peptides of SEQ ID No: 2 and SEQ ID No: 3, as is evident from FIGS. 2 to 5.

FIG. 2 shows the antimicrobial effect on the four pathogens mentioned by the DCD-eGFP fusion protein (from concentrated supernatant) with an incubation time of 4 h. The left-hand bar corresponds in each case to an amount of 0.1 µg/ml peptide, the middle bar to an amount of 1 µg/ml and the right-hand bar to an amount of 10 µg/ml.

Figure 3:
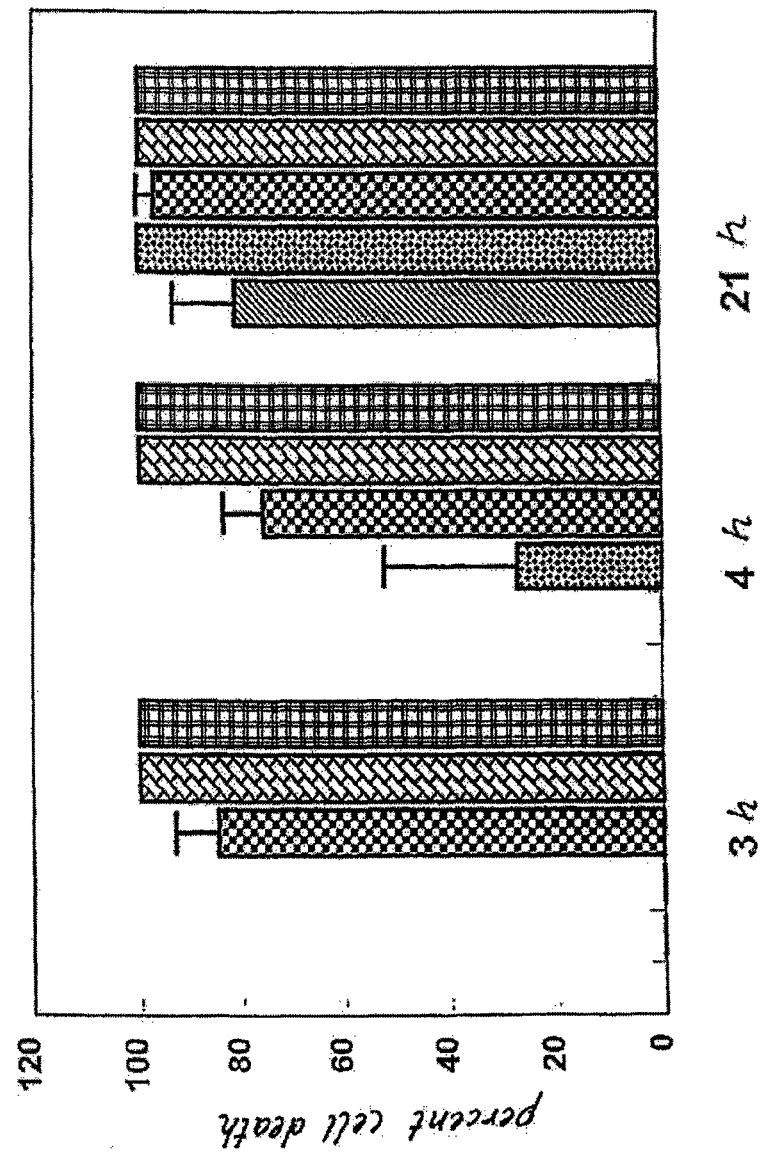
FIG. 3 in a bar diagram and an experimental approach as in FIG. 2 the antimicrobial effect of the peptide of SEQ ID No: 2.

FIG. 3 shows the antimicrobial effect on the four pathogens mentioned by the peptide of SEQ ID No: 2 on incubation for 4 h, with the four bars from left to right respectively corresponding to an amount of 1, 10, 50 and 100 µg/ml.

Figure 4:
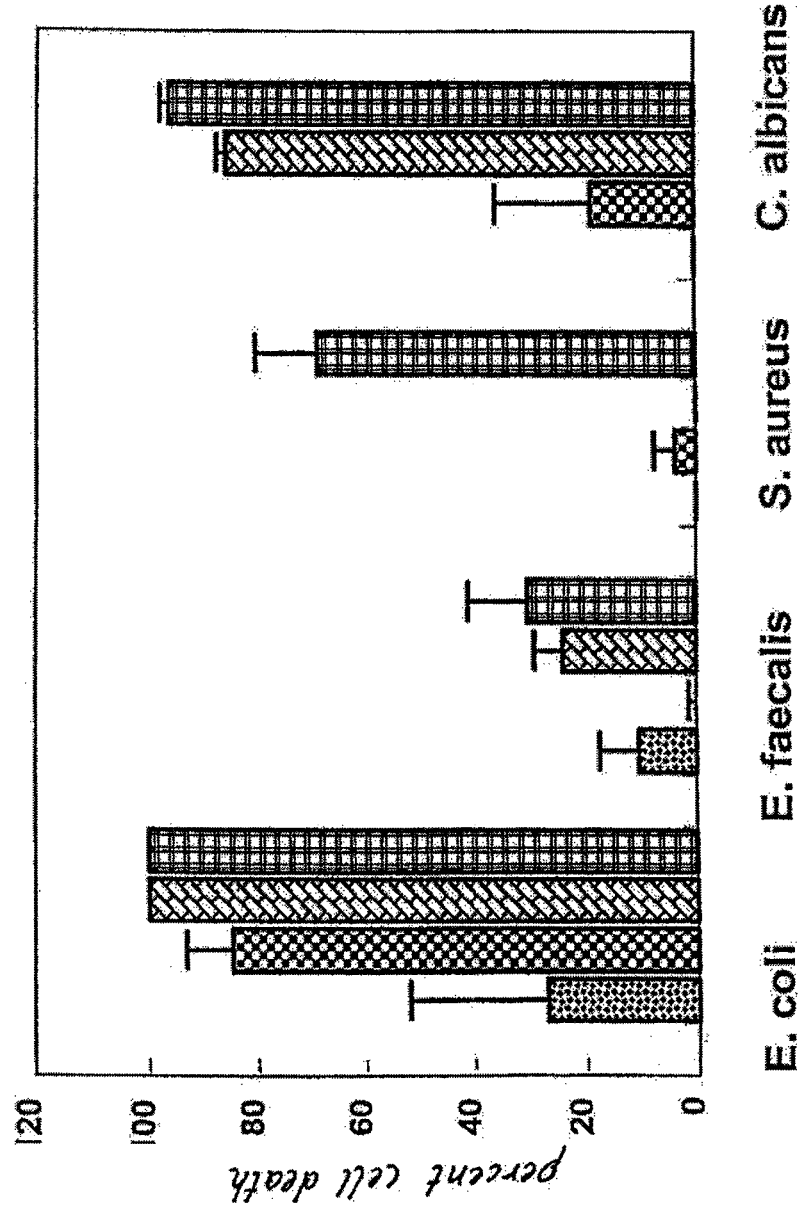
FIG. 4 in a bar diagram the quantity-dependent and incubation time-dependent antimicrobial effect of the peptide of SEQ ID No: 2 on E. coli.

FIG. 4 shows the time-dependent effect of the peptide of SEQ ID No: 2 on *E. coli*, with the five bars from left to right respectively corresponding to an amount of 0.1, 1, 10, 50 and 100 µg/ml.

Figure 5:
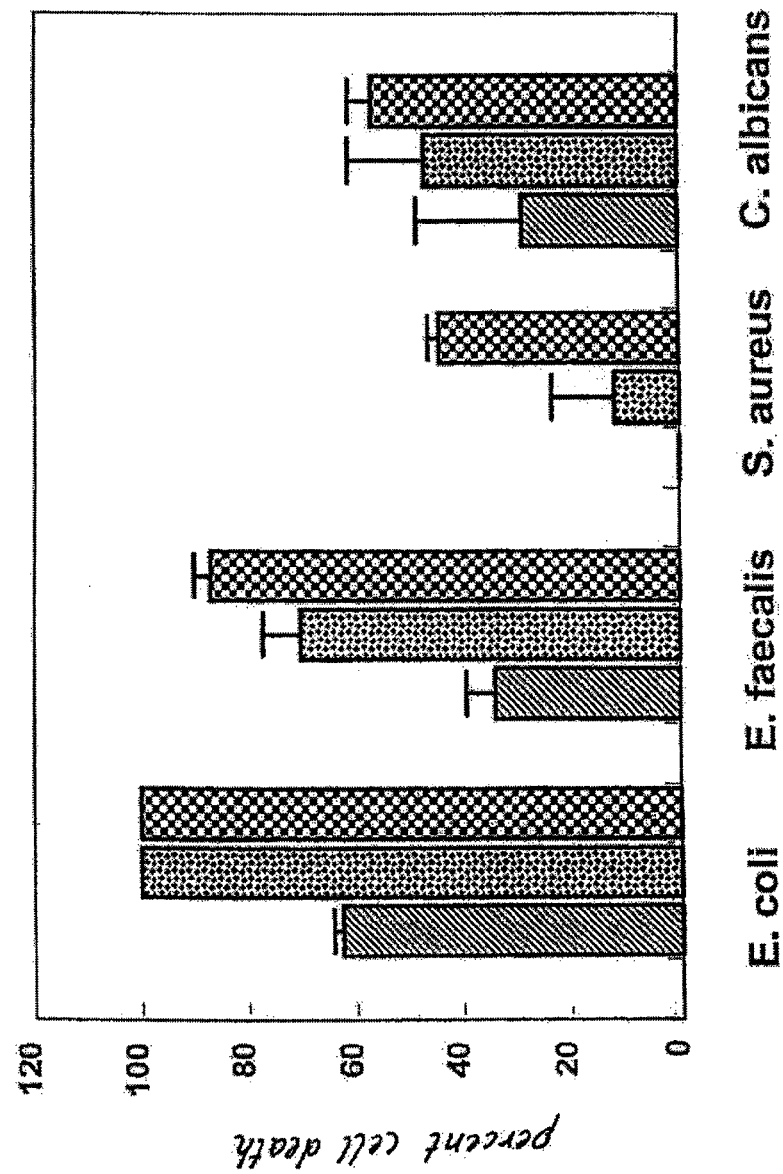
FIG. 5 in a bar diagram and an experimental approach as in FIG. 3 the antimicrobial effect of the peptide of SEQ ID No: 3.

Finally, FIG. 5 shows, comparably to FIG. 2, the antimicrobial effect of the peptide of SEQ ID No: 3 from the HPLC fraction on incubation for 3 h and 4 h. The two left-hand bars correspond in each case to an amount of 2.5 µg/ml and the two right-hand bars in a group correspond in each case to an amount of 25 µg/ml of peptide employed. The first and third bar in a group correspond in each case to an incubation time of 3 h, and the second and fourth bar in a group correspond in each case to an incubation time of 4 h.

It is evident from FIGS. 2 to 5 that all three tested peptides display a marked antimicrobial effect even when the amounts of peptide employed corresponds to the amount of DCD in sweat (1-10 μg/ml).

It is evident from the above that DCD and fragments of DCD display an antimicrobial effect on various pathogens, for example Gram-positive and Gram-negative bacteria, and yeasts. Since DCD and the fragments of DCD are secreted in sweat and, together with the latter, reach the surface of the skin, said peptides are particularly suitable for the curative or protective treatment of the skin because their natural site of action is evidently there.

Further investigations revealed an extended antimicrobial spectrum of DCD peptides, including *Staphylococcus epidermidis* (Vuong, C. et al. 2004 *Cell Microbiol.* 6:269-275), *Pseudomonas putida*, methicillin-resistant *S. aureus*, rifampin- and isoniazid-resistant *Mycobacterium tuberculosis* (Lai, Y. P. et al. 2005 *Biochem. Biophys. Res. Commun.* 328:243-250), and *Listeria monocytogenes* and *Salmonella enterica* serovar *Typhimurium* (Cipakova, I. et al. 2006 *Protein Expr. Purif.* 45:269-274).

Example 5

By postsecretory proteolytic processing in sweat the dermcidin protein gives rise to several truncated DCD peptides which differ in length and net charge. In order to understand the mechanism of antimicrobial activity, we analyzed the spectrum of activity of several naturally processed dermcidin-derived peptides, the secondary structure in different solvents, and the ability of these peptides to interact with or permeabilize the bacterial membrane. Interestingly, although all naturally processed DCD peptides can adopt an α-helical conformation in solvents, they have a diverse and partially overlapping spectrum of activity against gram-positive and gram-negative bacteria. This indicates that the net charge and the secondary structure of the peptides are not important for the toxic activity. Furthermore, using carboxyfluorescein-loaded liposomes, membrane permeability studies and electron microscopy we investigated whether DCD peptides are able to permeabilize bacterial membranes. The data convincingly show that irrespective of charge the different DCD peptides are not able to permeabilize bacterial membranes. However, bacterial mutants lacking specific cell envelope modifications exhibited different susceptibilities to killing by DCD peptides than wild-type bacterial strains. Finally, immunoelectron microscopy studies indicated that DCD peptides are able to bind to the bacterial surface; however, signs of membrane perturbation were not observed. These studies indicate that DCD peptides do not exert their activity by permeabilizing bacterial membranes.

Peptide synthesis and purification. Peptides were synthesized utilizing the Fmoc (9-fluorenylmethoxy carbonyl)/tBu chemistry using a multiple peptide synthesizer Syro II (MultiSynTech, Witten, Germany). After cleavage, the crude peptide was purified by HPLC on a reversed-phase C18 Nucleosil 100-5C column to a purity of >95% using a linear gradient of 5 to 80% acetonitrile in 0.05% trifluoroacetic acid for 45 min. All peptides were characterized by matrix-assisted laser desorption ionization-time of flight mass spectroscopy (MALDI-TOF-MS) and electrospray ionization and were in all cases in agreement with the calculated masses.

Antimicrobial assays. Antimicrobial assays were performed using the CFU assay as previously described (Rieg, S. et al. 2005 *J. Immunol.* 174:8003-8010, Schittek, B. et al. 2001 *Nat. Immunol.* 2:1133-1137). The antibacterial activity of DCD-derived peptides and LL-37 was tested against the following bacterial strains: *Escherichia coli* ATCC 25922, methicillin-susceptible *Staphylococcus aureus* ATCC 25923 (MSSA), methicillin-resistant *Staphylococcus aureus* (MRSA; clinical isolate), *Staphylococcus epidermidis* ATCC 12228, and *Pseudomonas aeruginosa* ATCC 27853. *E. coli* ML-35p was generously provided by Robert Lehrer (Department of Medicine, Center for Health Sciences, Los Angeles, Calif.) and cultivated on Luria-Bertani (LB) plates containing 50 μg of ampicillin/ml. This strain constitutively expresses cytoplasmic β-lactosidase but lacks lactose permease (Lehrer, R. I. et al. 1988 *J. Immunol. Methods* 108:153-158). The bacterial membrane mutants *Staphylococcus aureus* mprF and dltA and *Staphylococcus epidermidis* Δica and the corresponding wild-type strains *S. aureus* 113 and *S. epidermidis* 1457 were previously described (Gotz, F. 2002 *Mol. Microbiol.* 43:1367-1378, Peschel, A. et al. 2001 *J. Exp. Med.* 193:1067-1076). Bacterial cultures were grown to mid-exponential growth phase and washed three times with 10 mM sodium phosphate buffer-10 mM NaCl (pH 7.0). The bacterial concentration was estimated photometrically at 600 nm. Absorbance of 1.0 corresponded to $8.56 \times 10^8$/ml for *E. coli*; $1 \times 10^8$/ml for *E. coli* ML-35p; $1.97 \times 10^8$/ml for *S. aureus*, MRSA, and the wild-type and membrane mutants of *S. aureus* and *S. epidermidis*; and $5.07 \times 10^8$/ml for *P. aeruginosa*.

After dilution to a concentration of $10^6$ CFU/ml, 10-μl portions of the dilutions were incubated at 37° C. for 2 to 4 h with the respective peptide diluted in water in a total volume of 30 μl in 10 mM sodium phosphate buffer-10 mM NaCl (pH 7.0). After incubation, the cells were diluted 1:100 in 10 mM sodium phosphate buffer-10 mM NaCl (pH 7.0), and 90 μl of the diluted bacterial suspension was plated in triplicates on blood agar. Bacterial colonies were counted after incubation for 18 to 24 h at 37° C. The antimicrobial activity was calculated by using [(cell survival after peptide incubation)/(cell survival in buffer without peptide)×100]. The $LC_{90}$ describes the lethal concentration of the current synthetic peptide in μg/ml or μM that leads to a 90% reduction of CFU compared to the buffer control.

Membrane permeabilization. To examine the effects of DCD-derived peptides and LL-37 to permeabilize the inner membrane of gram-negative bacteria, we used a previously described method using the permease-deficient strain *E. coli* ML-35p, which constitutively expresses cytoplasmic β-galactosidase (Lehrer, R. I. et al. 1989 *J. Clin. Investig.* 84:553-561, Lehrer, R. I. et al. 1988 *J. Immunol. Methods* 108:153-158). Bacteria were grown for 18 h at 37° C. and washed three times with 10 mM sodium phosphate buffer (pH 7.0) and resuspended in this buffer to $10^8$ CFU/ml. Then, 100 μl of the bacterial suspension was pipetted into a cuvette containing 70 μl of 20 mM sodium phosphate buffer (pH 7.0) and 30 μl of 30 mM β-galactosidase substrate ONPG (o-nitrophenyl-β-D-galactopyranoside) in 20 mM sodium phosphate and 100 μl of the test peptide solution. The production of o-nitrophenol (ONP) over time was monitored spectrophotometrically at a wavelength of 420 nm. An equivalent volume of water replaced the peptide solution in the control assay.

Outer membrane (OM) permeability was assessed by using *E. coli* ML-35p by 1-N-phenyl-naphtylamine (NPN; Sigma-Aldrich, Germany) uptake assay as already described (Loh, B. et al. 1984 *Antimicrob. Agents Chemother.* 26:546-551). This hydrophobic probe fluoresces strongly in phospholipid environments but only weakly in an aqueous environment. Normally, intact OM excludes hydrophobic molecules, but through the action of permeabilizers, the phospholipids become accessible and allow NPN access into the phospholipid layer. Thus, increased fluorescence in NPN-containing bacterial suspensions indicates OM damage. E. coli ML-35p was incubated with DCD-derived peptides or LL-37. EDTA as a chelating agent was used as a control. NPN was prepared as a 0.5 mM acetone stock solution and diluted freshly in 5 mM HEPES buffer (pH 7.2) to a concentration of 10 µM. Cells were grown to the logarithmic phase in LB medium and were washed twice in 5 mM HEPES buffer (pH 7.2) and resuspended in the same buffer to an optical density ($A_{600}$) of 0.5. Next, 50 µl of the bacterial suspension was added to a 96-microwell plate containing 5 mM HEPES buffer (23 µl), test peptide solution (25 µl), and 2 µl of 0.5 mM NPN. The permeabilization of outer membrane was monitored by measuring the increase in fluorescence intensity at 460 nm with excitation at 355 nm in a spectrofluorophotometer (Tecan SPECTRAFluor, Crailsheim, Germany). The results are expressed as NPN uptake factors, which was calculated as a quotient of background-corrected fluorescence and the highest fluorescence value.

Preparation of liposomes and CF release assay. Large unilamellar vesicles made of 1,2-dioleoyl-sn-glycero-3-phosphocholine (DOPC) and 1,2-dioleoyl-sn-glycero-3-phosphoglycerol (DOPG)-DOPC at a 1:1 molar ratio were used in liposome lysis and CD measurements and prepared as already described (Mayer, L. D. et al. 1986 *Biochim. Biophys. Acta* 858:161-168). Phospholipids were purchased from Avanti-Polar Lipids (Alabaster, Ala.). Phospholipid stock solutions (2 µmol) were dissolved in $CHCl_3$-MeOH (2:1) and then dried in an exsiccator by vacuum. Multilamellar liposomes were formed by hydrating the dry lipids at room temperature with 600 µl of 50 mM MES (morpholineethanesulfonic acid)-50 mM $K_2SO_4$ (pH 6.5) containing 50 mM carboxyfluorescein (CF; Sigma, Steinheim, Germany) to encapsulate it into liposomes for CF release assay and with 600 µl of 10 mM sodium phosphate buffer (pH 7.0) for CD measurement. Multilamellar liposomes were freeze-thawed 10 times to enhance encapsulation. In order to get unilamellar liposomes, multilamellar liposomes were extruded 10 times through two stacked 400-nm-pore-size polycarbonate membranes (Isopore membrane filters; Millipore). The CF-entrapped vesicles were separated from free carboxyfluorescein by gel filtration using Sephadex G-50 columns. The liposome concentration was determined by phosphorous analysis (Rouser, G. et al. 1970 *Lipids* 5:494-496). The liposomal preparations were kept at 4° C. and used within a few hours.

The release of CF from liposomes was measured by monitoring the increase in fluorescence intensity at 515 nm with excitation at 492 nm in a RF-5301 PC Spectrofluorophotometer (Schimadzu). CF release was initiated by addition of known concentrations of DCD peptide or LL-37 (1 to 10 µM) into a magnetically stirred cuvette containing the CF-loaded liposomes (25 µM phospholipid/ml) in 1.5 ml of assay buffer. CF release was expressed as the percentage of CF released relative to the fluorescence released after addition of 20 µl of a 20% Triton X-100 solution at the end of each experiment.

Preparation of unilamellar vesicles for carboxyfluorescein efflux experiments. Large unilamellar vesicles were prepared for CF experiments by the extrusion technique (Mayer, L. D. et al. 1986 *Biochim. Biophys. Acta* 858:161-168). Fluorescence measurements were recorded using a RF-5301 spectrophotometer (Shimadzu).

CF-loaded vesicles were prepared with 50 mM CF and then diluted in 1.5 ml of $K^+$ buffer (50 mM MES-KOH [pH 6.0], 100 mM $K_2SO_4$) in a final concentration of 25 µM phospholipid on a phosphorous base. After addition of the peptide, the increase of fluorescence intensity was measured at 520 nm (excitation at 492 nm) at room temperature. Peptide induced leakage was documented relative to the total amount of marker release after solubilization of the vesicles by the addition of 10 µl of 20% Triton X-100.

CD) spectroscopy. Circular dichroism (CD) measurements were performed with a Jasco J-720 CD spectrapolarimeter (Jasco, Tokyo, Japan) to determine the secondary structure of DCD-derived peptides. The data are reported as the average of three to four scans at 50 nm/min with a 1-nm step resolution. The CD spectra of the peptides (50 µM) in 10 mM sodium phosphate buffer (pH 7.0) with different amounts of NaCl (10, 100, and 150 mM) in 0 to 60% (vol/vol) trifluoroethanol (TFE) and in the presence of artificial phospholipid vesicles such as DOPC and DOPC-DOPG (1:1 molar ratio) were recorded at room temperature in the 180- to 260-nm wavelength range. The data are reported as the mean residue ellipticity in units of degrees $cm^2$ $dmol^{-1}$ and plotted versus wavelength. The secondary structural predictions for peptides were carried out by Jasco secondary structure software.

Aggregation assay. Labeling of the N terminus of DCD-1L, SSL-23, and LL-37 with fluorescein isothiocyanate (FITC) was achieved by elongation of the N-terminal bound peptide with β-alanine and afterwards by FITC. The molecular mass was determined by MALDI-MS analysis and agreed with the calculated mass. Oligomerization of the peptides in solution was determined by fluorescence dequenching as previously described (Oren, Z. et al. 1999 *Biochem. J.* 341(Pt. 3):501-513). Fluorescein-labeled peptides (stock solution 10 µM in 1× phosphate-buffered saline [PBS] pH 7.4) were added at different concentrations (0.0625 to 0.5 µM) to a white 96-well plate (final volume, 100 µl; Nunc, Wiesbaden, Germany). For the determination of the time-kinetics of oligomerization, peptides were incubated for different time points (0 to 220 min) at room temperature in PBS before proteinase K (50 µg/ml; Sigma) was added to each peptide. For the estimation of the correlation of the peptide concentration and the aggregation state, the peptides were preincubated 2 h in PBS before proteinase K treatment. Enzyme treatment resulted in an increase in the fluorescence emission as a result of the dequenching of the FITC fluorescence. Excitation was set at 485 nm, and emission was set at 535 nm on a spectrofluorophotometer (Tecan SPECTRAFluor; Crailsheim, Germany). Fluorescence measurements were performed in triplicates at room temperature.

Western blot analysis. After physical exercise sweat of the forehead was collected and analyzed by Western blot as already described (Rieg, S. et al. 2006 *J. Investig. Dermatol.* 126:354-365). Briefly, sweat was centrifuged 3 min at 13,000 rpm (16,000×g) to remove particles and frozen. Then, 15-µl portions of the samples and 4 µg of the DCD peptides LEK-45 and DCD-1L dissolved in water were separated by sodium dodecyl sulfate-polyacrylamide gel electrophoresis (using 15% acrylamide with 0.05% bisacrylamide), transferred electrophoretically (1200 mA/h) onto polyvinylidene difluoride membrane sheets (Immobilon-PSQ; Millipore, Germany) with a tank type blotter and then blocked in 10% nonfat milk in PBS (pH 7.4) for 30 min at room temperature. After incubation with a rabbit polyclonal anti-DCD antibody (1:2,000) that detects the C terminus of DCD-1L overnight at 4° C., the membrane sheets were washed with phosphate buffer and incubated with an anti-rabbit secondary biotin-conjugated polyclonal antibody (1:1,500 in blocking solution). After washing in phosphate buffer the Streptavidin-AP-conjugate (Roche, Mannheim, Germany) was used for the detection of biotin-labeled secondary antibody. The membrane was immersed in CDP-Star solution (Western Lightning chemiluminescence reagents for AP; Roche) for 10 min and then exposed to X-ray film (Eastman Kodak, Rochester, N.Y.).

Hemolytic assay. The hemolytic activity of DCD peptides was determined on fresh human erythrocytes, which were separated from human EDTA blood using a Ficoll gradient. Isolated erythrocytes were washed three times in 5 ml of PBS (50 mM sodium phosphate buffer, 150 mM NaCl [pH 7.0]) and centrifuged at 1,000×g for 6 min at room temperature. The pellets were resuspended in PBS and further diluted to a concentration of $10^9$ human erythrocytes/ml. Hemolytic activity was determined as follows. To the human erythrocyte solution (50 µl), PBS (1 ml) was added, followed by different concentrations of the peptides. The suspension was incubated for 30 min at 37° C. and then centrifuged at 1,000×g for 6 min at 4° C. The supernatant was monitored at 415 nm by using a spectrophotometer (Bio-Rad, Munich, Germany). The hemolytic activity of each peptide was expressed as the percentage of the total hemoglobin release compared to the release after incubation with Millipore water.

TEM and IEM. Liquid cultures of S. aureus (ATCC 25923) cells grown up to mid-logarithmic phase were washed twice in 10 mM sodium phosphate buffer (pH 7.4). Cells ($10^8$ CFU) were treated with DCD-1 or SSL-23 (100 µg/ml) for 4 h at 37° C. In parallel, antimicrobial assays with both peptides were performed which confirmed the antibacterial activity of both peptides. For immune electron microscopy (IEM), cells were fixed in PLP and centrifuged, and the resulting bacterial pellet was embedded in 3.5% agarose at 37° C. and cooled on ice. Small parts of agarose blocks were embedded in Lowicryl (Polysciences, Eppelheim, Germany). Ultrathin sections (50 nm) were mounted on Formvar-coated nickel grids and incubated with rabbit anti-DCD, followed by 10-nm gold-conjugated goat anti-rabbit immunoglobulin G (Auroprobe EM; Amersham, Freiburg, Germany). In control samples the primary antibody was omitted. Samples were examined by using a Zeiss 109 transmission electron microscope (Zeiss, Oberkochen, Germany). For transmission EM (TEM) bacterial pellets were fixed in Karnovsky's fixative, postfixed in 1% osmium tetroxide, and embedded in Epon.

Results

Figure 6:
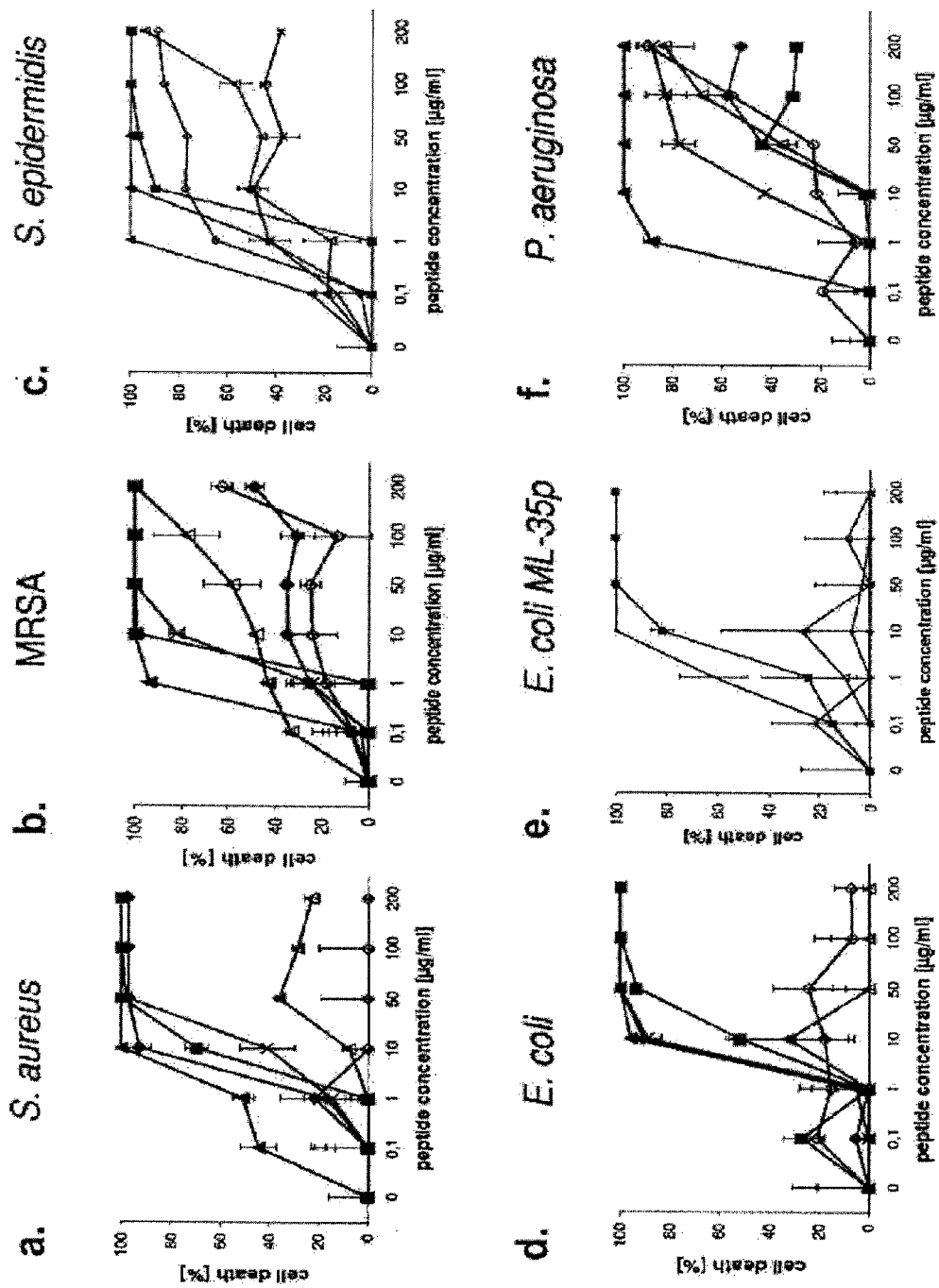
FIG. 6. Antimicrobial activity of DCD-derived peptides against several bacterial strains. The concentration-dependent antimicrobial activity of the DCD-derived peptides DCD-1L (■), LEK-45 (Δ), SSL-29 (◊), SSL-25 (+), SSL-23 (♦), and LL-37 (▲) on the bacterial strains: (a) S. aureus, (b) MRSA, (c) S. epidermidis, (d) E. coli, (e) E. coli ML-35p, and (f) Pseudomonas aeruginosa after 2 to 3 h of incubation in 10 mM phosphate buffer-10 mM NaCl (pH 7.0) is presented. The number of bacterial colonies were counted, and the percentage of cell death calculated as described in Example 4 (see also Schittek, B. et al. 2001 Nat. Immunol. 2:1133-1137). The microbicidal activity was expressed as [1−(cell survival after peptide incubation)/(cell survival after control peptide incubation)]×100, which represents the percentage killing of the cells.

DCD-derived peptides have a diverse and overlapping spectrum of antimicrobial activity. We previously showed (Flad, T. et al. 2002 J. Immunol. Methods 270:53-62) that several DCD-derived peptides are generated in human eccrine sweat by postsecretory proteolytic processing. First, we wanted to address the question whether the alteration from anionic to cationic peptides during proteolytic processing of DCD-1L leads to a different spectrum of antimicrobial activity. For this purpose, we performed antimicrobial assays with the most prominent DCD-derived peptides found in human eccrine sweat: DCD-1L and LEK-45 (both anionic), SSL-29 (neutral net charge), and SSL-25 and SSL-23 (both cationic). As a positive control peptide, we used the cathelicidin LL-37 and as a negative control peptide the unrelated scrambled peptide DPI (Table 1). The concentration-dependent antimicrobial activities of the DCD peptides are shown in FIG. 6, and the 90% inhibitory concentrations are summarized in Table 2. Interestingly, the different DCD peptides demonstrate different spectra of activity. Whereas the anionic peptide DCD-1L and the cationic derivatives SSL-25 and SSL-23 show antibiotic activity against most tested microorganisms (E. coli, S. aureus MSSA and MRSA, and S. epidermidis) ($IC_{90}$<50 µg/ml), the DCD-derived peptides LEK-45 and SSL-29 show in most cases only minimal inhibitory activity against the tested microorganisms or only at higher peptide concentrations ($IC_{90}$>180 µg/ml). Interestingly, SSL-25 and SSL-23 show similar or even better antibacterial activity than the parental peptide DCD-1L on the majority of the tested microorganisms. However, in contrast to DCD-1L, they possess only limited activity against S. epidermidis and MRSA, respectively (see Table 2 and FIG. 6). Furthermore, all tested DCD peptides show only a low level of antibacterial activity against P. aeruginosa. Our study demonstrates that the naturally processed DCD peptides have a different spectrum of activity and that DCD peptides exhibit antimicrobial activity irrespective of their charge. Since LEK-45 and further N-terminal-shortened derivatives have a significantly lower activity than the parental peptide DCD-1L, it seem that at least the first three amino acids SSL are important for the antimicrobial function. Furthermore, since the peptides SSL-23 and SSL-25 show antibacterial activity similar to that of DCD-1L, this indicates that the minimal region responsible for antimicrobial activity lies in the range of the first 23 amino acids of the DCD-1L peptide. Interestingly, a peptide with a few additional amino acids and a neutral net charge (SSL-29) lost the ability to kill several microorganisms (see FIG. 6 and Table 2).

TABLE 1

Amino acid sequence and biochemical properties of DCD-derived peptides and control peptides used in this study

| Peptide | Amino acid sequence | Charge/pI |
|---|---|---|
| DCD peptides | | |
| DCD-1L | SSLLEKGLDGAKKAVGGLGKLGKDAVEDLESV GKGAVHDVKDVLDSVL (SEQ ID NO: 8) | −2/5.07 |
| DCD-1 | SSLLEKGLDGAKKAVGGLGKLGKDAVEDLESV GKGAVHDVKDVLDSV (SEQ ID NO: 9) | −2/5.07 |
| LEK-45 | LEKGLDGAKKAVGGLGKLGKDAVEDLESVGKG AVHDVKDVLDSVL (SEQ ID NO: 10) | −2/5.08 |
| SSL-29 | SSLLEKGLDGAKKAVGGLGKLGKDAVEDL (SEQ ID NO: 11) | 0/5.97 |
| SSL-25 | SSLLEKGLDGAKKAVGGLGKLGKDA (SEQ ID NO: 12) | +2/9.4 |
| SSL-23 | SSLLEKGLDGAKKAVGGLGKLGK (SEQ ID NO: 13) | +3/9.82 |
| Control peptides | | |
| DPI | DPYAEAASGPNPGSKSHESAQAENCGADPE (SEQ ID NO: 14) | −5/4.08 |
| LL-37 | LLGDFFRKSKEKIGKEFKRIVQRIKDFLRNLVP RTES (SEQ ID NO: 15) | +6/10.6 |

TABLE 2

Antimicrobial activities of DCD-derived peptides and, as a control peptide, LL-37 on different microorganisms and bacterial mutants

| Microorganism | DCD-1L | LEK-45 | SSL-29 | SSL-25 | SSL-23 | LL-37 |
|---|---|---|---|---|---|---|
| Gram-positive bacteria | | | | | | |
| S. aureus (MSSA) | 45 (9.3) | >200 (>44) | >200 (>69) | 48 (19.9) | 10 (4.5) | 9 (2.0) |
| S. aureus (MRSA) | 8 (1.7) | 180 (40) | >200 (>69) | 35 (14.5) | >200 (>89) | 0.9 (0.2) |
| S. epidermidis | 10 (2.1) | 200 (44) | 200 (69) | >200 (>80) | 8 (3.6) | 0.9 (0.2) |
| Gram-negative bacteria | | | | | | |
| E. coli | 45 (9.3) | >200 (>44) | >200 (>69) | 10 (4.1) | 10 (4.5) | 9 (2.0) |
| E. coli ML-35p | 30 (6.2) | >200 (>44) | >200 (>69) | 9 (3.7) | ND | ND |
| P. aeruginosa | >200 (>41) | >200 (>44) | >200 (>69) | 200 (83) | >200 (>89) | 1 (0.2) |
| Bacterial mutants | | | | | | |
| S. aureus 113 wild type | 180 (35) | >200 (>44) | >200 (>69) | >200 (>82) | >75 (>33) | 6 (1.3) |
| S. aureus mprF | 50 (10) | >200 (>44) | 180 (>62) | >200 (>82) | 50 (22) | 6 (1.3) |
| S. aureus dltA | 6 (1.2) | >200 (>44) | ND | >200 (>82) | 10 (4.5) | 6 (1.3) |
| S. epidermidis 1457 wild type | 50 (10) | >200 (>44) | >200 (>69) | 6 (2.5) | >200 (>89) | 9 (2.0) |
| S. epidermidis Δica | >200 (>41) | >200 (>44) | ND | ND | >200 (>89) | 9 (2.0) |

[a]The 90% inhibitory concentration ($IC_{90}$) is the concentration of peptide in μg/ml (or in μM [in parentheses]) able to kill 90% of the microorganisms in 10 mM NaP-10 mM NaCl in a CFU assay compared to the control incubated only in buffer without peptide. ND, not determined.

Conformational studies. For several antimicrobial peptides (AMPs), a close correlation between the antimicrobial activity and an α-helical secondary structure of the peptide has been described (Brogden, K. A. 2005 Nat. Rev. Microbiol. 3:238-250). DCD-1L is able to arrange in an amphipathic α-helical conformation. To examine the secondary structure of the different DCD-derived peptides, we performed CD measurements of DCD-1L, LEK-45, SSL-29, SSL-25, and SSL-23 and the control peptides DPI and LL-37 in different solutions. As shown in Table 3, when the DCD peptides were dissolved in aqueous buffer such as water or sodium phosphate buffer, no α-helicity was observed and all peptides had predominantly a random coil secondary structure. This did not change when the peptides were incubated in a buffer with a NaCl concentration of up to 150 mM. In contrast, the human cathelicidin LL-37 presented a 50% α-helical content already in 10 mM sodium phosphate buffer. Furthermore, to simulate the contact of the peptides with a bacterial membrane, we incubated the DCD peptides with unilamellar liposomes that differ in charge due to the content of artificial phospholipids such as DOPC and DOPG-DOPC (1:1 molar ratio) in sodium phosphate buffer. Neither the cationic nor the anionic DCD peptides adopted an α-helix under these conditions, in contrast to LL-37, where the α-helical secondary structure increased from 50 to 80% upon contact with the negatively charged liposomes (Table 3). Similar results for the different DCD peptides were achieved after incubation with S. aureus. Interestingly, all DCD-derived peptides can adopt an α-helix in the presence of increasing concentrations of TFE, although to different extents. Whereas DCD-1L and LEK-45 displayed in the presence of 60% TFE 34 and 28% α-helical contents, respectively, SSL-29, SSL-25, and SSL-23 demonstrated 12, 31, and 14% α-helical content, respectively (Table 3). Since, in contrast to DCD-1L, SSL-25, and SSL-23, the DCD-derived peptides LEK-45 and SSL-29 show a diminished antimicrobial activity on the microorganisms tested (see Table 2), there was no clear relationship between the α-helical content of N and C terminally truncated DCD-1L analogs with their antimicrobial activity.

TABLE 3

Summary of the CD analysis of several DCD-derived and control peptides in different solutions: distilled water, 10 mM sodium phosphate (NaP), 10 mM NaP with 10 or 150 mM NaCl, TFE, or in the presence of unilamellar liposomes, such as DOPC and DOPC-DOPG (1:1 molar ratio)[a]

| Peptide | Solution | Secondary structure (%) | | | |
|---|---|---|---|---|---|
| | | α-Helix | β-Sheet | Turn | Random coil |
| DCD-1L | dH₂O | 0.0 | 28.8 | 16.4 | 54.9 |
| | 10 mM NaP | 0.0 | 17.5 | 20.5 | 62.0 |
| | 10 mM NaP-10 mM NaCl | 0.0 | 19.1 | 19.4 | 61.4 |
| | 10 mM NaP-150 mM NaCl | 0.0 | 32.1 | 0.0 | 67.9 |
| | DOPC | 0.0 | 35.2 | 9.8 | 55.0 |
| | DOPC-DOPG | 0.0 | 27.8 | 15.4 5 | 6.8 |
| | 60% TFE | 34.5 | 27.2 | 0.0 | 38.3 |
| LEK-45 | dH₂O | 0.0 | 30.3 | 16.1 | 53.6 |
| | 10 mM NaP | 0.0 | 13.6 | 21.2 | 62.2 |
| | 10 mM NaP-10 mM NaCl | 0.0 | 17.0 | 19.5 | 63.5 |
| | 10 mM NaP-150 mM NaCl | 0.0 | 41.5 | 0.0 | 58.5 |
| | 60% TFE 2 | 8.0 | 31.0 | 0.0 | 41.0 |
| SSL-23 | dH₂O | 0.0 | 38.2 | 14.8 | 47.0 |
| | 10 mM NaP | 0.0 | 23.8 | 18.4 | 57.7 |
| | DOPC | 0.0 | 13.7 | 21.5 | 64.8 |
| | DOPC-DOPG | 2.2 | 49.2 | 3.8 | 44.8 |
| | 60% TFE | 14.1 | 40.8 | 4.9 | 49.2 |
| | 80% TFE | 32.9 | 27.6 | 0.0 | 39.5 |
| SSL-25 | dH₂O | 0.0 | 22.3 | 20.7 | 57.0 |
| | 60% TFE | 31.1 | 27.1 | 0.0 | 41.8 |
| SSL-29 | dH2O | 0.0 | 24.3 | 20.3 | 55.4 |
| | 60% TFE | 12.2 | 46.2 | 0.0 | 41.7 |
| LL-37 | 10 mM NaP | 50.9 | 6.0 | 16.6 | 26.5 |
| | DOPC | 54.1 | 6.4 | 14.0 | 25.5 |
| | DOPC-DOPG | 80.2 | 0.0 | 8.7 | 11.0 |
| DPI | dH₂O | 0.0 | 34.3 | 15.4 | 50.3 |
| | 10 mM NaP | 0.0 | 25.8 | 19.4 | 54.8 |
| | DOPC-DOPG | 0.0 | 29.7 | 19.1 | 51.2 |
| | 60% TFE | 9.6 | 42.0 | 6.0 | 42.5 |

[a]Data are based on Jasco secondary structure estimation software. dH₂O, distilled water.

Figure 7:
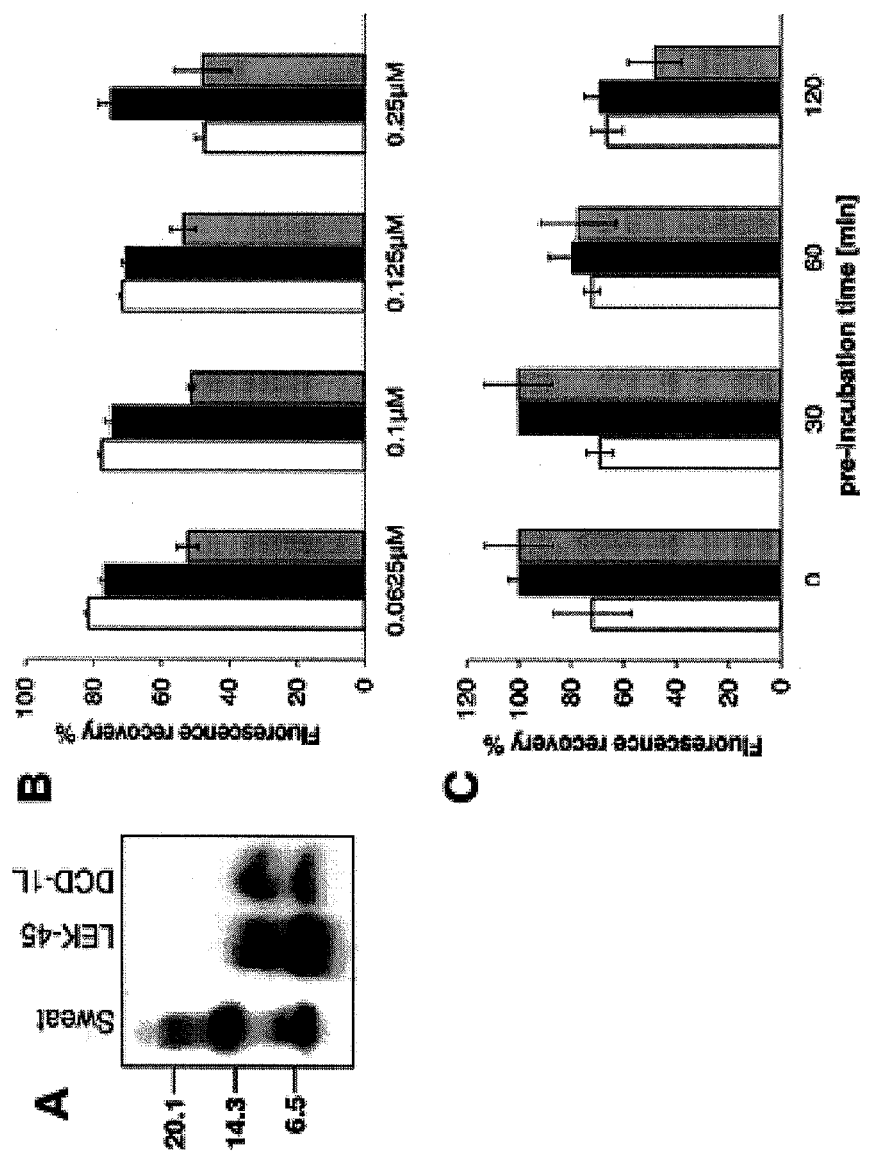
FIG. 7. Determination of the oligomerization of the peptides DCD-1L, LEK-45, SSL-23, and LL-37 in solution. (A) Sodium dodecyl sulfate-polyacrylamide gel electrophoresis and Western blot analysis of human eccrine sweat and 4 µg of the DCD peptides LEK-45 and DCD-1L dissolved in water using a polyclonal anti-DCD antibody, which detects the C terminus of DCD-1L. Seen are SDS-stable dimers for LEK-45 and DCD-1L and higher oligomers in sweat. (B) Percent fluorescence recovery of FITC-labeled peptides LL-37 (□), DCD1L (■), and SSL-23 (▨) in 1×PBS (pH 7.4) at different concentrations (0.0625 to 0.25 µM). Peptides were preincubated 2 h in PBS before proteinase K (10 µg/ml) treatment. Oligomerization of the peptides in solution was determined by fluorescence dequenching. (C) Determination of the time-kinetics of oligomerization: peptides (0.25 µM) were incubated for different time points (0 to 120 min) at room temperature in PBS before proteinase K treatment, and the percentage of fluorescence recovery was determined.

DCD-1L self-associates in solution. In human sweat several sodium dodecyl sulfate-stable oligomers of DCD peptides are found in a Western blot analysis with an anti-DCD antiserum (FIG. 7A). Interestingly, the synthetic peptides DCD-1L and LEK-45 (FIG. 7A) are also able to form SDS-stable dimers. These data indicate that DCD-1L and LEK-45 are able to self-associate.

Furthermore, to investigate the ability of DCD-1L and the shortened form SSL-23 to self-associate in solution, we used FITC-labeled peptides. As a control peptide we used FITC-labeled LL-37. We used the fluorescence quenching assay described by Oren et al. (Oren, Z. et al. 1999 Biochem. J. 341:501-513). This assay is based on the principle that the fluorescence is quenched when several molecules are in close proximity, i.e., when they self-associate or form oligomers. The fluorescence of the respective peptide at different concentrations is compared to the fluorescence of the peptide after treatment with proteinase K, which resulted in total degradation of the peptides (the 100% value). The percentage of fluorescence recovery of the peptide in solution is a measurement of the aggregation state. As seen in FIGS. 7B and C, DCD-1L and SSL-23 self-associates in PBS in a time-dependent, but not concentration-dependent, manner. The fluorescence dropped successively to 70 and 50% of the fluorescence after protease treatment for DCD-1L and SSL-23, respectively, after 2 h. In contrast, LL-37 was able to self-associate concentration dependently up to 50%. In contrast to DCD-1L, however, a stable fluorescence level was achieved already from the earliest time point analyzed (FIG. 7C). This indicates that the DCD peptides DCD-1L and SSL-23 can self-associate but that it takes approximately 2 h to achieve this.

Kinetics of antimicrobial activity. To analyze the time kinetics of antimicrobial activity, we incubated DCD-1L for 30, 60, 120, or 180 min with S. aureus or E. coli and analyzed the number of CFU after the respective time points. As shown in FIG. 8A, it takes approximately 2 h for DCD-1L to kill the majority of gram-positive and gram-negative bacteria (FIG. 8A) in a concentration-dependent manner. After 1 h of incubation with DCD-1L, the bacterial cell number is reduced; however, killing was significantly increased after 2 and 3 h of incubation with the peptide. This is in contrast to incubation of the bacteria with LL-37, which results in an immediate decrease in bacterial cell numbers (FIG. 8A). This may point to different mechanisms of activity of LL-37 and DCD-1L.

Figure 8B:
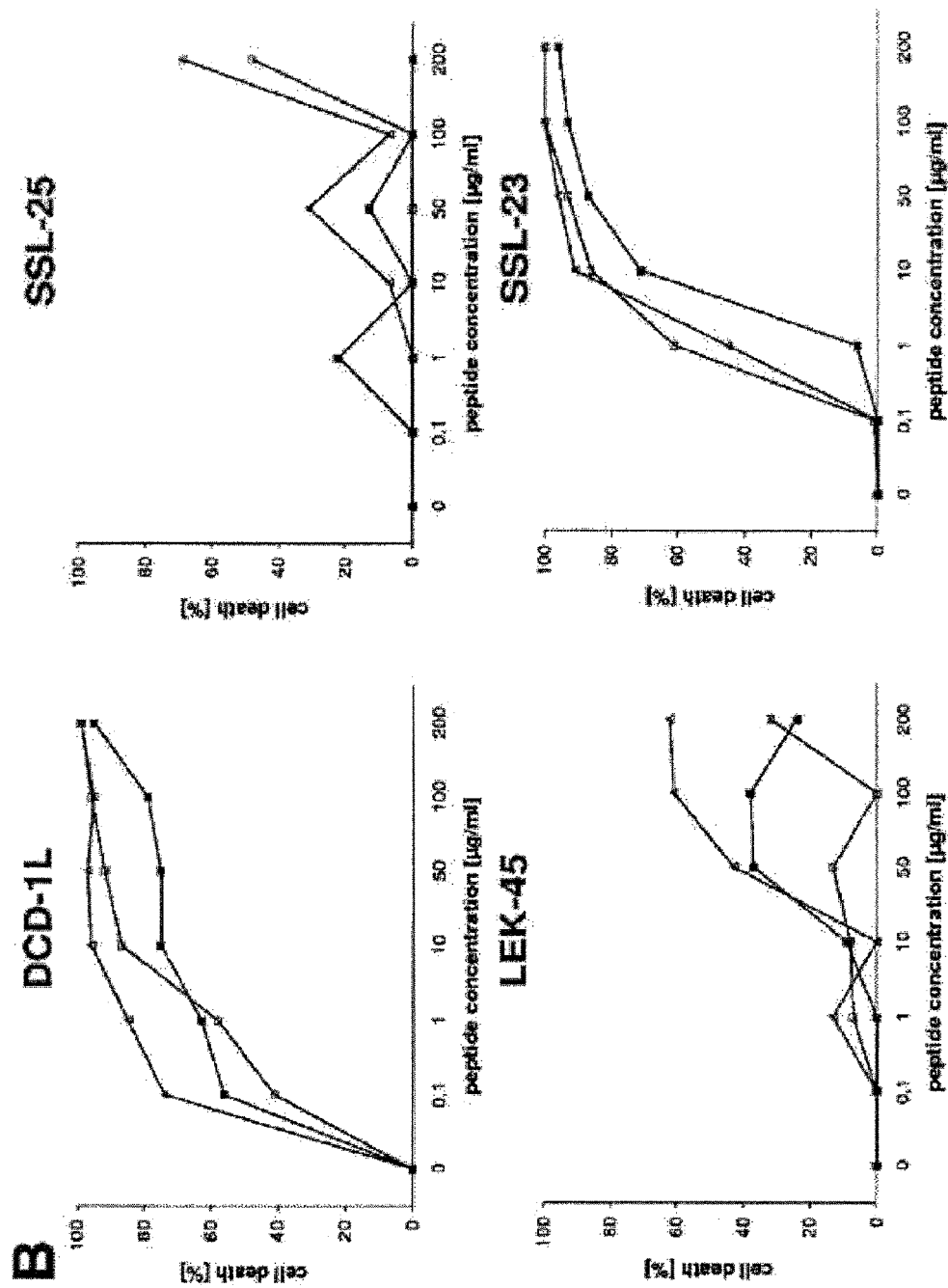
FIG. 8. Time kinetics and antimicrobial activity of DCD-derived peptides against bacterial cell envelope mutants. (A) Time-dependent killing of S. aureus (■) and E. coli (♦) by DCD-1L using the CFU assay. Bacteria in the mid-logarithmic phase of growth were incubated with DCD-1L (200 µg/ml, black symbols) at different time intervals (0-180 min). The open squares indicate the antimicrobial activity of the control peptide LL-37 (100 µg/ml). (B) S. aureus cell envelope mutants mprF (□) and dltA (Δ) and wild-type SA113 (■) were incubated with various concentrations of peptides (0.1 to 200 µg/ml) in 10 mM phosphate buffer-10 mM NaCl (pH 7.0) for 2 to 3 h at 37° C. Aliquots of bacterial suspensions were diluted and plated in triplicate on blood agar. The percentage of cell death was determined as described above. (C) S. epidermdis Δica and wild-type S. epidermidis 1457 were incubated with various concentrations of peptides (0.1 to 200 µg/ml) in 10 mM phosphate buffer-10 mM NaCl (pH 7.0) for 2 to 3 h at 37° C., and the percentage of cell death was determined as described above.
Figure 8C:
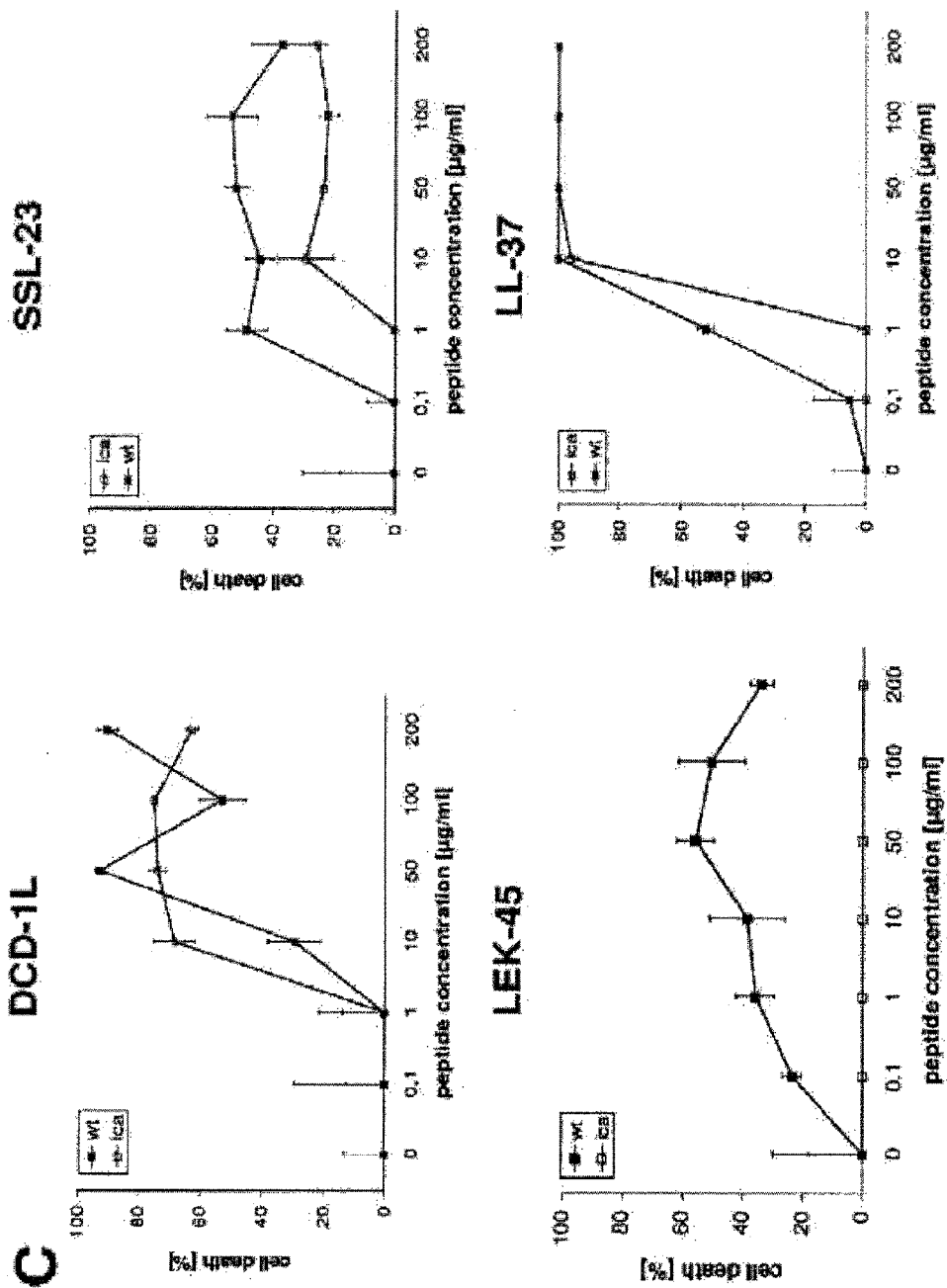

Antimicrobial activity against bacterial cell envelope mutants. To analyze whether bacterial membrane mutants lacking specific cell envelope modifications are more susceptible to cationic and anionic DCD-derived peptides, we performed antimicrobial assays with the S. aureus mutants mprF and dltA, the S. epidermidis mutant Δica, and the corresponding wild-type strains. As can be seen in FIG. 8B and Table 2, the S. aureus mutants mprF and dltA are more sensitive to DCD-derived peptides, especially the dltA mutant. Furthermore, whereas LEK-45 and SSL-29 did not kill wild-type bacteria up to a concentration of 200 µg/ml, both peptides are able to kill the mutants at high concentrations. In contrast, the ica mutant seemed to be less sensitive to DCD peptides than the wild-type S. epidermidis strain (FIG. 8C and Table 2). These data indicate that gram-positive bacterial mutants with specific modifications in the bacterial envelope exhibit altered susceptibilities to the DCD-derived peptides.

Permeabilization of the outer and inner membrane of gram-negative bacteria. Since many antibacterial peptides exert their effect by perturbing the permeability properties of the inner or outer membrane in gram-negative bacteria, we examined the effect of DCD-derived peptides on the integrity of the cytoplasmic and outer membrane of E. coli.

The activity of DCD peptides on the inner membrane of E. coli was investigated by monitoring the leakage of cytoplasmic β-galactosidase in the strain E. coli ML-35p as described by Lehrer et al. (Lehrer, R. I. et al. 1989 J. Clin. Investig. 84:553-561). Only when the cytoplasmic membrane is permeabilized by AMPs can the activity of cytoplasmic β-galactosidase be detected extracellularly by the hydrolysis of the substrate ONPG into ONP. The release of ONP was monitored spectrophotometrically at 420 nm. As shown in FIG. 9B, the DCD peptides DCD-1L, LEK-45, SSL-29, SSL-25, and SSL-23 at a concentration of 100 µg/ml did not permeabilize the inner membrane of E. coli ML-35p over a time period of more than 3 h, although DCD-1L and SSL-25 are highly active against this strain (see Table 2). In contrast, the cathelicidin LL-37 permeabilized the inner membrane of E. coli ML-35p after a few minutes at a concentration of 10 µg/ml.

Next, we investigated whether DCD-derived peptides are able to permeabilize the outer membrane of E. coli ML-35p. For this purpose, we incubated the DCD peptides DCD-1L, LEK-45, SSL-29, SSL-25, and SSL-23 at a concentration of 200 µg/ml with E. coli ML-35p. Permeabilization of the outer membrane was measured by an increase in the fluorescence of NPN. The outer membrane normally excludes hydrophobic molecules such as NPN unless it is damaged. In this case, NPN can get access to the hydrophobic membrane interior, which results in an increase in NPN fluorescence. As shown in FIG. 9A, incubation of E. coli ML-35p with 200 µg/ml of the DCD peptides DCD-1L, LEK-45, SSL-29, SSL-25, and SSL-23 did not result in significant NPN uptake compared to a buffer control with the same amount of NPN. In contrast, LL-37 permeabilized the outer membrane of E. coli ML-35p in a few minutes (FIG. 9A). These data indicate that—in contrast to LL-37—cationic and anionic DCD peptides did not permeabilize the inner and outer membranes of E. coli ML-35p.

Interaction with phospholipid bilayers. By using a model membrane system such as CF-loaded liposomes, we wanted to assess the mechanisms of natural peptide activity. The DCD peptides DCD-1L, LEK-45, and SSL-23 and, as a control, the irrelevant peptide DPI were tested for their ability to interact with phospholipid bilayers. We used unilamellar liposomes of different lipid compositions and charges: DOPC (neutral) and DOPC-DOPG (1:1 molar ratio) (50% negatively charged phospholipids). An increase in fluorescence intensity corresponds to CF release and is indicative of liposome leakage or lysis (Breukink, E. et al. 1997 Biochemistry 36:6968-6976). In FIG. 9 it is shown that DCD-derived peptides caused only weak leakage (<13%) from liposomes made of DOPC (FIG. 9C) and DOPC-DOPG (FIG. 9D) even after the addition of 10 µM peptide. In contrast, LL-37 caused a rapid release of CF in the first minute. LL-37 induced CF efflux from the DOPC liposomes was lower (~39%) (FIG. 9C) than from DOPC-DOPG liposomes with a negative charged surface (~73%) (FIG. 9D). Incubation of the liposomes with the irrelevant peptide DPI resulted in very low CF release ($\leq$2%). These data demonstrate that DCD-derived peptides do not permeabilize unilamellar liposomes made of different lipid compositions as bacterial model membranes. This indicates that the antimicrobial activity of DCD peptides is not due to pore formation or a destabilization of the bacterial membrane.

Figure 10:
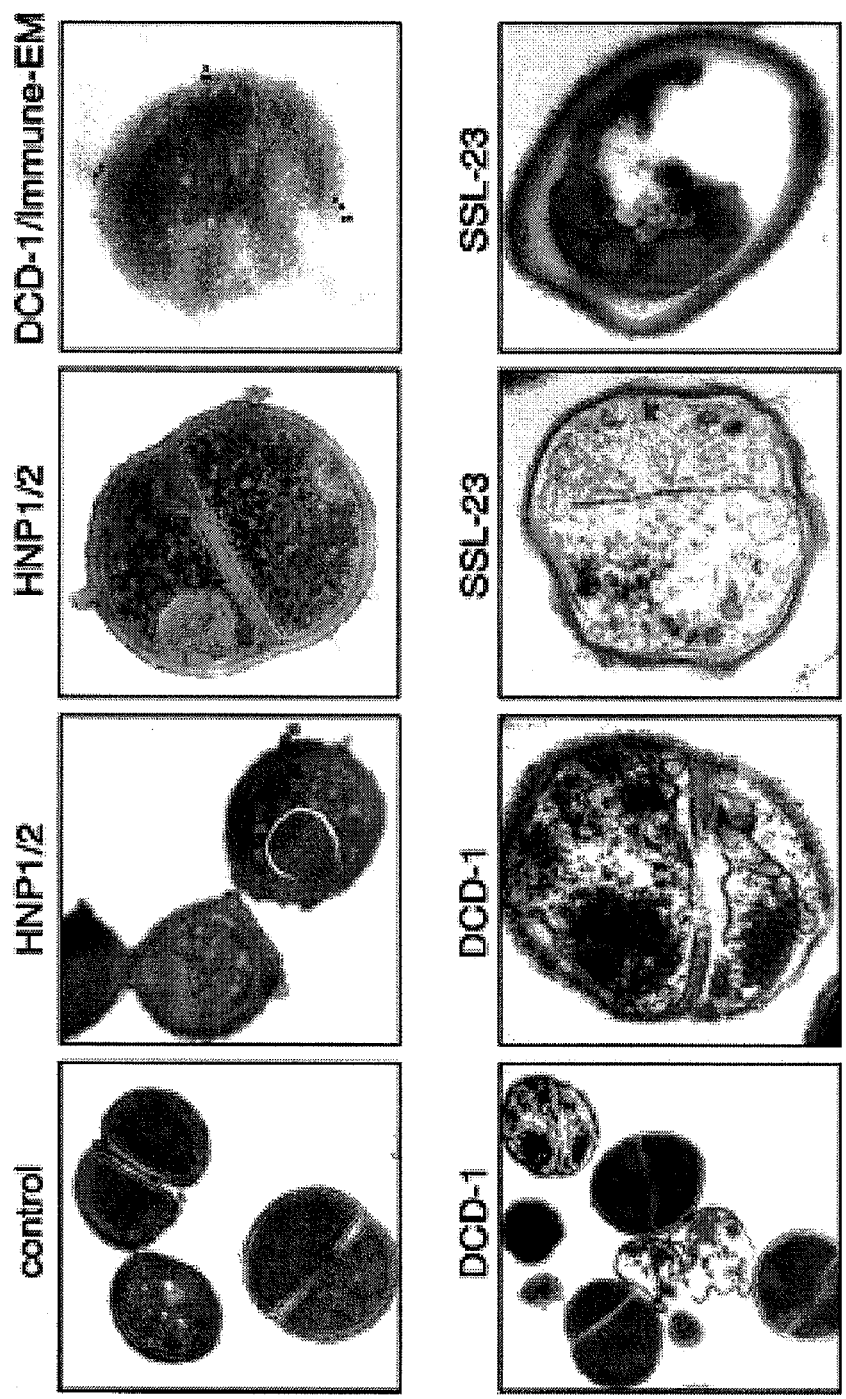
FIG. 10. Morphology of peptide-treated S. aureus. Transmission EM and immune-EM of S. aureus (ATCC 25923) treated with either DCD-1, SSL-23, or the alpha-defensins HNP-1 and -2 as a positive control for pore formation in 10 mM sodium phosphate buffer. Bacteria were incubated with 100 µg of DCD-1, SSL-23, and HNP1/2 per ml for 4 h. As a negative control cells were incubated in buffer without peptide. For the immune-EM, bacteria were incubated with a polyclonal antiserum to DCD-1, and the reactivity was detected by immunogold labeling. Seen is the binding of DCD to the bacterial surface.

Morphological changes. The experiments described above indicated that DCD peptides did not kill gram-negative bacteria by permeabilization of the bacterial membranes. To investigate how DCD peptides kill gram-positive bacteria, we examined the morphological changes of S. aureus by using transmission EM after incubation with 100 µg of the antimicrobially active DCD peptides DCD-1 or SSL-23/ml for 4 h. As shown in FIG. 10, we found no signs of cell wall damage. Instead, we observed cellular disintegration, suggesting that the anionic DCD-1 and cationic SSL-23 kill these bacteria by some unknown mechanism that does not initially disrupt their cytoplasmic membrane. In contrast, the alpha-defensins HNP-1/2 induced membrane blebbing of S. aureus as already described (Lehrer, R. I. et al. 1989 J. Clin. Investig. 84:553-561, Selsted, M. E. et al. 2005 Nat. Immunol. 6:551-557) (FIG. 10). Bacteria from the control culture (FIG. 10) did not show any detectable deformation or alteration of the membrane or the cytoplasm. Furthermore, to investigate whether DCD-1 binds to the bacterial surface or is found in the cytoplasm, we performed immune-EM using an antiserum to DCD-1. As shown in FIG. 10, DCD-1 is able to bind to the cell surface but is not found in the bacterial cytoplasm.

Hemolytic activity. Since several cationic AMPs have been described to have cytotoxic activity against eukaryotic cells, we analyzed whether DCD peptides are able to lyse eukaryotic cells. Therefore, we incubated the DCD peptides DCD-1L, LEK-45, SSL-29, SSL-25, and SSL-23 with human erythrocytes and analyzed photometrically the hemolytic activity. The DCD peptides did not exhibit hemolytic activity up to a concentration of 100 µg/ml. Similar results were obtained for LL-37: little hemolytic activity (up to 2.5%) was seen at a high LL-37 concentration (100 µg/ml). These data indicate that DCD-derived peptides do not damage the membranes of either prokaryotic or eukaryotic cells.

Until now, more than 700 AMPs have been isolated from diverse species such as plants, amphibians, insects, and mammals (Beisswenger, C. et al. 2005 Curr. Protein Peptide Sci. 6:255-264). Despite diverse structural motifs, a common feature of most of these peptides is that they are cationic and form amphipathic structures (Hancock, R. E. et al. 1998 Trends Biotechnol. 16:82-88). Cationic AMPs display a net positive charge ranging from +2 to +9. It is believed that the charge is important for the initial electrostatic attraction of AMPs to negatively charged phospholipid membranes of bacteria or other microorganisms (Brogden, K. A. 2005 Nat. Rev. Microbiol. 3:238-250, Yeaman, M. R. et al. 2003 Pharmacol. Rev. 55:27-55). Cell death due to cationic AMPs may begin as quickly as 2 to 3 min after initial exposure (Blondelle, S. E. et al. 1999 Biochim. Biophys. Acta 1462:89-108, Hancock, R. E. et al. 1999 Antimicrob. Agents Chemother. 43:1317-1323, Lehrer, R. I. et al. 1989 J. Clin. Investig. 84:553-561, Tossi, A. et al. 1997 Eur. J. Biochem. 250:549-558). It has been primarily attributed to membrane perturbation due to pore formation, membrane permeabilization, or depolarization of the bacterial membrane that leads to the loss of ions and metabolites, the cessation of essential vital functions, and ultimately to cell death (Gazit, E. et al. 1995 Biochemistry 34:11479-11488, Heller, W. T. et al. 2000 Biochemistry 39:139-145, Matsuzaki, K. 1998 Biochim. Biophys. Acta 1376:391-400).

We previously showed that by postsecretory proteolytic processing in sweat the dermcidin gene product gives rise to a whole group of truncated DCD peptides (Flad, T. et al. 2002 J. Immunol. Methods 270:53-62). Interestingly, proteolytically processed DCD peptides possess net charges between −2 and +2. DCD-1L and DCD-1 exhibit antimicrobial activity against gram-positive organisms, including S. aureus, E. faecalis, and gram-negative organisms including E. coli (Yeaman, M. R. et al. 2003 Pharmacol. Rev. 55:27-55), as well as against S. epidermidis (Vuong, C. et al. 2004 Cell Microbiol. 6:269-275), Pseudomonas putida, MRSA, and rifampin- and isoniazid-resistant M. tuberculosis (Lai, Y. P. et al. 2005 Biochem. Biophys. Res. Commun. 328:243-250). In the present study we show that the cationic truncated DCD peptides SSL-25 and SSL-23 additionally exhibit antimicrobial activity against several gram-positive and gram-negative bacteria, including MRSA, with a similar spectrum of activity than the parental peptide DCD-1L. This indicates that the net charge of the DCD peptides is not essential for the antimicrobial function. However, the DCD peptide SSL-29 with four additional amino acids compared to SSL-25 and which has a neutral charge did not kill any of the microorganisms analyzed up to a concentration of 200 µg/ml. This indicates that the charge of the DCD peptide, irrespective of a positive or negative net charge, is essential either for binding to the bacterial membrane or for structure formation. Furthermore, a peptide lacking the first N-terminal three amino acids (SSL) from the DCD-1L sequence is not able to kill the microorganisms analyzed. Our comprehensive analysis furthermore suggested that the active part of the DCD-1L sequence resides in the first 23 amino acids.

Membrane permeability studies with gram-negative bacteria or liposomes as model bacterial membranes indicated that all DCD peptides did not permeabilize the bacterial membrane in contrast to the cathelicidin LL-37. The same seems to be the case for eukaryotic cells such as red blood cells since we see no hemolysis up to a concentration of 100 µg/ml, which is in agreement with a previous publication (Lai, Y. P. et al. 2005 Biochem. Biophys. Res. Commun. 328:243-250). Time kinetics indicated that the killing of bacteria by DCD peptides is a rather slow process, taking at least 2 h in vitro. This is in contrast to LL-37, which is able to kill the bacteria by membrane permeabilization after the first few minutes. Interestingly, analysis of the ability of DCD-1L and SSL-23 to aggregate indicated that it also takes approximately 2 h to self-associate to a stable plateau. The ability to form oligomers was also seen in vivo in human sweat. These data indicate that DCD-1L has to form stable complexes in order to kill microorganisms. Aggregation occurs most likely in solution or on the bacterial membrane. Indeed, our studies indicate that the bacterial membrane interacts with DCD peptides. Immune-EM studies showed that DCD-1 binds to the bacterial surface in clusters. Furthermore, the bacterial envelope mprF and dltA mutants lacking cell envelope modifications are more sensitive to the activity of DCD peptides irrespective of the charge of the latter. Therefore, we suggest a model in which negatively or positively charged DCD peptides form oligomers, which in turn bind to the bacterial membrane without causing massive permeabilization. Binding to and possibly insertion into the membrane may impair vital functions to such an extent that the system gets highly stressed and eventually out of balance. Interaction with defined targets outside and possibly also inside the bacteria may enforce the stress and finally result in cell death. It may be that DCD peptides act similar to the non-membrane-permeabilizing AMPs already described (Brogden, K. A. 2005 Nat. Rev. Microbiol. 3:238-250, Otvos, L., Jr. 2005 J. Peptide Sci. 11:697-706, Yeaman, M. R. et al. 2003 Pharmacol. Rev. 55:27-55).

Although DCD is able to form multimers in solution, it is unclear which structure is necessary for the antimicrobial activity and whether DCD peptides have to multimerize in lipid membranes to achieve the toxic activity on microorganisms. We could show that all analyzed DCD peptides, irrespective of charge or activity, can adopt an alpha-helical conformation in helix-inducing solvents. These data are in agreement with the determination of the secondary structure of recombinant DCD-1L (Lai, Y. P. et al. 2005 Biochem. Biophys. Res. Commun. 328:243-250). Whereas in buffer or after incubation with artificial phospholipid membranes for more than 2 h DCD peptides have mainly a random structure, the alpha-helical content of LL-37 rapidly increased after incubation with negatively charged liposomes. These data indicate that in contrast to LL-37 the secondary structure does not correlate with the antimicrobial activity of DCD peptides. A number of models for membrane permeation by amphipathic alpha-helical peptides have been described, in some of them aggregation or oligomerization of the peptides seems to be important for disrupting the membranes of the target cells (Johansson, J. et al. 1998 *J. Biol. Chem.* 273:3718-3724, Oren, Z. et al. 1999 *Biochem. J.* 341(Pt. 3):501-513). Many AMPs exist in relatively unstructured conformations prior to interaction with the target cell. Upon binding to bacterial membranes, peptides may undergo significant conformational dynamics to helical or other structures that affect antimicrobial activity (Brogden, K. A. 2005 *Nat. Rev. Microbiol.* 3:238-250).

Gram-positive bacteria, such as staphylococci, are distinguished by the presence of a thick cell wall composed of peptidoglycan and teichoic acid polymers and the absence of an outer membrane (Peschel, A. 2002 *Trends Microbiol.* 10:179-186). *S. aureus* mutants lacking specific modifications in the bacterial membrane are highly susceptible to a variety of cationic AMPs. For example, incorporation of D-alanine into *S. aureus* teichoic acids by the dltA enzymes (Peschel, A. et al. 1999 *J. Biol. Chem.* 274:8405-8410) or the lysylation of phosphatidylglycerol by mprF (Staubitz, P. et al. 2004 *FEMS Microbiol. Lett.* 231:67-71) confers resistance to defensins, protegrins, and other AMPs by repulsion of the cationic peptides. Disruption of the dltA or mprF gene in *S. aureus* increases the susceptibility to several cationic AMPs such as defensins, protegrins, or amphibian magainin (Peschel, A. et al. 2001 *J. Exp. Med.* 193:1067-1076, Peschel, A. et al. 1999 *J. Biol. Chem.* 274:8405-8410). Furthermore, mutations in the ica operon in *S. epidermidis*, the genes responsible for the biosynthesis of the slime polymer polysaccharide intercellular adhesin, reduces the formation of a biofilm, and increases the sensitivity of *S. epidermidis* to cationic AMPs (Gotz, F. 2002 *Mol. Microbiol.* 43:1367-1378, Vuong, C. et al. 2004 *Cell Microbiol.* 6:269-275). Interestingly, we could show that the dltA and mprF mutants are susceptible to cationic and anionic DCD peptides, i.e., irrespective of charge of the peptide. In contrast, the ica mutant seemed to be less sensitive to DCD peptides than the wild-type *S. epidermidis* strain. It has been reported that by increasing the salt concentration of the incubation buffer, the efficacy of DCD-1L against the ica mutant is increased (Vuong, C. et al. 2004 *Cell Microbiol* 6:269-275). This could indicate that a complex is formed between DCD peptides and salt ions which increases the ability to kill bacteria. We could show that DCD-1L and DCD-1 are also active under high-salt conditions and in a buffer resembling human sweat (Schittek, B. et al. 2001 *Nat. Immunol.* 2:1133-1137). Furthermore, our own experiments indicated that DCD-1L has a higher killing activity in a buffer with 10 mM NaCl compared to phosphate buffer alone. Increasing the salt concentration up to 150 mM did not alter the activity. In a recently published study it was shown that the ionic environment dictates microbial susceptibility to AMPs (Dorschner, R. A. et al. 2006 *FASEB J.* 20:35-42). Therefore, it is possible that under the complex conditions in human sweat the antimicrobial activity of DCD peptides is much higher than under the in vitro conditions used in this study.

In conclusion, in human eccrine sweat several dermcidin-derived peptides are generated by postsecretory proteolytic processing. Some of the dominant peptides such as DCD-1L, DCD-1, SSL-46 (Rieg, S. et al. 2005 *J. Immunol.* 174:8003-8010), SSL-25, and SSL-23 have a diverse and overlapping spectrum of antimicrobial activity, whereas the other dominant peptides in sweat such as LEK-45 and SSL-29 found also in the majority of sweat samples (Rieg, S. et al. 2006 *J. Investig. Dermatol.* 126:354-365) are inactive. Thus, by postsecretory proteolytic processing the immune response against skin pathogens is modulated.

What is claimed is:

1. An isolated and purified antimicrobially active peptide fragment from the C-terminus of dermcidin (DCD) protein of SEQ ID NO: 1, wherein the antimicrobially active peptide consists of a maximum of 50 contiguous amino acid residues from the C-terminal of DCD, and wherein the peptide comprises amino acids 66-85 of SEQ ID NO: 1.

2. A method for treating human skin against microorganisms, comprising the step of administering the antimicrobially active peptide fragment of claim 1.

3. A pharmaceutical composition which comprises as active ingredient antimicrobially active peptide fragment of claim 1 in an antimicrobially effective amount, and further comprises a carrier suitable for pharmaceutical administration.

4. A cosmetic composition which comprises as active ingredient antimicrobially active peptide fragment of claim 1 in an antimicrobially effective amount, and further comprises a carrier suitable for cosmetic application.

5. An isolated fragment of SEQ ID NO: 2, said fragment comprising amino acids 4-23 of SEQ ID NO: 2, with the proviso that said fragment is not SEQ ID NO: 3, or a fusion protein comprising said fragment.

6. A fragment of SEQ ID NO: 1, comprising SEQ ID NO: 3, or a fusion protein comprising said fragment.

* * * * *

SEQUENCE LISTING

<160> NUMBER OF SEQ ID NOS: 161

<210> SEQ ID NO 1
<211> LENGTH: 110
<212> TYPE: PRT
<213> ORGANISM: Homo sapiens

<400> SEQUENCE: 1

```
Met Arg Phe Met Thr Leu Leu Phe Leu Thr Ala Leu Ala Gly Ala Leu
 1               5                  10                  15

Val Cys Ala Tyr Asp Pro Glu Ala Ala Ser Ala Pro Gly Ser Gly Asn
            20                  25                  30

Pro Cys His Glu Ala Ser Ala Ala Gln Lys Glu Asn Ala Gly Glu Asp
        35                  40                  45

Pro Gly Leu Ala Arg Gln Ala Pro Lys Pro Arg Lys Gln Arg Ser Ser
    50                  55                  60

Leu Leu Glu Lys Gly Leu Asp Gly Ala Lys Lys Ala Val Gly Gly Leu
65                  70                  75                  80

Gly Lys Leu Gly Lys Asp Ala Val Glu Asp Leu Glu Ser Val Gly Lys
                85                  90                  95

Gly Ala Val His Asp Val Lys Asp Val Leu Asp Ser Val Leu
            100                 105                 110
```

<210> SEQ ID NO 2
<211> LENGTH: 48
<212> TYPE: PRT
<213> ORGANISM: Artificial Sequence
<220> FEATURE:
<223> OTHER INFORMATION: synthetic fragment of DCD protein

<400> SEQUENCE: 2

```
Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45
```

<210> SEQ ID NO 3
<211> LENGTH: 47
<212> TYPE: PRT
<213> ORGANISM: Artificial Sequence
<220> FEATURE:
<223> OTHER INFORMATION: synthetic fragment of DCD protein

<400> SEQUENCE: 3

```
Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val
        35                  40                  45
```

<210> SEQ ID NO 4
<211> LENGTH: 30
<212> TYPE: PRT
<213> ORGANISM: Artificial Sequence
<220> FEATURE:
<223> OTHER INFORMATION: synthetic peptide

<400> SEQUENCE: 4

```
Tyr Asp Pro Glu Ala Ala Ser Ala Pro Gly Ser Gly Asn Pro Cys His
 1               5                  10                  15

Glu Ala Ser Ala Ala Gln Lys Glu Asn Ala Gly Glu Asp Pro
            20                  25                  30
```

<210> SEQ ID NO 5
<211> LENGTH: 30
<212> TYPE: PRT
<213> ORGANISM: Artificial Sequence
<220> FEATURE:
<223> OTHER INFORMATION: synthetic peptide

<400> SEQUENCE: 5

```
Asp Pro Tyr Ala Glu Ala Ala Ser Gly Pro Asn Pro Gly Ser Lys Ser
 1               5                  10                  15

His Glu Ser Ala Gln Ala Glu Asn Cys Gly Ala Asp Pro Glu
            20                  25                  30
```

<210> SEQ ID NO 6
<211> LENGTH: 458
<212> TYPE: DNA
<213> ORGANISM: Homo Sapiens

<400> SEQUENCE: 6

```
gaccctagat cccaagatct ccaaggattt ggtggcatac ccactccagc acacagaagc    60
```

```
atgaggttca tgactctcct cttcctgaca gctctggcag gagccctggt ctgtgcctat    120
gatccagagg ccgcctctgc cccaggatcg gggaaccctt gccatgaagc atcagcagct    180
caaaaggaaa atgcaggtga agacccaggg ttagccagac aggcaccaaa gccaaggaag    240
cagagatcca gccttctgga aaaaggccta gacggagcaa aaaaagctgt ggggggactc    300
ggaaaactag gaaaagatgc agtcgaagat ctagaaagcg tgggtaaagg agccgtccat    360
gacgttaaag acgtccttga ctcagtacta tagctgtaag gagaagctga gaaatgatac    420
ccaggagcag caggctttac gttttcagcc taaaacct                            458
```

<210> SEQ ID NO 7
<211> LENGTH: 24
<212> TYPE: PRT
<213> ORGANISM: Artificial Sequence
<220> FEATURE:
<223> OTHER INFORMATION: synthetic peptide

<400> SEQUENCE: 7

```
Lys Glu Asn Ala Gly Glu Asp Pro Gly Leu Ala Arg Gln Ala Pro Lys
1               5                   10                  15

Pro Arg Lys Gln Arg Ser Ser Leu
            20
```

<210> SEQ ID NO 8
<211> LENGTH: 48
<212> TYPE: PRT
<213> ORGANISM: Artificial sequence
<220> FEATURE:
<223> OTHER INFORMATION: synthetic peptide

<400> SEQUENCE: 8

```
Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45
```

<210> SEQ ID NO 9
<211> LENGTH: 47
<212> TYPE: PRT
<213> ORGANISM: Artificial Sequence
<220> FEATURE:
<223> OTHER INFORMATION: synthetic peptide

<400> SEQUENCE: 9

```
Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val
        35                  40                  45
```

<210> SEQ ID NO 10
<211> LENGTH: 45
<212> TYPE: PRT
<213> ORGANISM: Artificial Sequence
<220> FEATURE:
<223> OTHER INFORMATION: synthetic peptide

<400> SEQUENCE: 10

```
Leu Glu Lys Gly Leu Asp Gly Ala Lys Lys Ala Val Gly Gly Leu Gly
1               5                   10                  15
```

```
Lys Leu Gly Lys Asp Ala Val Glu Asp Leu Glu Ser Val Gly Lys Gly
             20                  25                  30

Ala Val His Asp Val Lys Asp Val Leu Asp Ser Val Leu
             35                  40                  45

<210> SEQ ID NO 11
<211> LENGTH: 29
<212> TYPE: PRT
<213> ORGANISM: Artificial Sequence
<220> FEATURE:
<223> OTHER INFORMATION: synthetic peptide

<400> SEQUENCE: 11

Ser Ser Leu Leu Glu Lys Gly Leu Asp Gly Ala Lys Lys Ala Val Gly
  1               5                  10                  15

Gly Leu Gly Lys Leu Gly Lys Asp Ala Val Glu Asp Leu
             20                  25

<210> SEQ ID NO 12
<211> LENGTH: 25
<212> TYPE: PRT
<213> ORGANISM: Artificial Sequence
<220> FEATURE:
<223> OTHER INFORMATION: synthetic peptide

<400> SEQUENCE: 12

Ser Ser Leu Leu Glu Lys Gly Leu Asp Gly Ala Lys Lys Ala Val Gly
  1               5                  10                  15

Gly Leu Gly Lys Leu Gly Lys Asp Ala
             20                  25

<210> SEQ ID NO 13
<211> LENGTH: 23
<212> TYPE: PRT
<213> ORGANISM: Artificial Sequence
<220> FEATURE:
<223> OTHER INFORMATION: synthetic peptide

<400> SEQUENCE: 13

Ser Ser Leu Leu Glu Lys Gly Leu Asp Gly Ala Lys Lys Ala Val Gly
  1               5                  10                  15

Gly Leu Gly Lys Leu Gly Lys
             20

<210> SEQ ID NO 14
<211> LENGTH: 30
<212> TYPE: PRT
<213> ORGANISM: Artificial Sequence
<220> FEATURE:
<223> OTHER INFORMATION: synthetic peptide

<400> SEQUENCE: 14

Asp Pro Tyr Ala Glu Ala Ala Ser Gly Pro Asn Pro Gly Ser Lys Ser
  1               5                  10                  15

His Glu Ser Ala Gln Ala Glu Asn Cys Gly Ala Asp Pro Glu
             20                  25                  30

<210> SEQ ID NO 15
<211> LENGTH: 37
<212> TYPE: PRT
<213> ORGANISM: Artificial Sequence
<220> FEATURE:
<223> OTHER INFORMATION: synthetic peptide

<400> SEQUENCE: 15
```

Leu Leu Gly Asp Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 16
<211> LENGTH: 23
<212> TYPE: PRT
<213> ORGANISM: Homo sapiens

<400> SEQUENCE: 16

Ser Ser Leu Leu Glu Lys Gly Leu Asp Gly Ala Lys Lys Ala Val Gly
1               5                   10                  15

Gly Leu Gly Lys Leu Gly Lys
            20

<210> SEQ ID NO 17
<211> LENGTH: 25
<212> TYPE: PRT
<213> ORGANISM: Homo sapiens

<400> SEQUENCE: 17

Ser Ser Leu Leu Glu Lys Gly Leu Asp Gly Ala Lys Lys Ala Val Gly
1               5                   10                  15

Gly Leu Gly Lys Leu Gly Lys Asp Ala
            20                  25

<210> SEQ ID NO 18
<211> LENGTH: 22
<212> TYPE: PRT
<213> ORGANISM: Homo sapiens

<400> SEQUENCE: 18

Ser Ser Leu Leu Glu Lys Gly Leu Asp Gly Ala Lys Lys Ala Val Gly
1               5                   10                  15

Gly Leu Gly Lys Leu Gly
            20

<210> SEQ ID NO 19
<211> LENGTH: 21
<212> TYPE: PRT
<213> ORGANISM: Homo sapiens

<400> SEQUENCE: 19

Ser Ser Leu Leu Glu Lys Gly Leu Asp Gly Ala Lys Lys Ala Val Gly
1               5                   10                  15

Gly Leu Gly Lys Leu
            20

<210> SEQ ID NO 20
<211> LENGTH: 20
<212> TYPE: PRT
<213> ORGANISM: Homo sapiens

<400> SEQUENCE: 20

Ser Ser Leu Leu Glu Lys Gly Leu Asp Gly Ala Lys Lys Ala Val Gly
1               5                   10                  15

Gly Leu Gly Lys
            20

```
<210> SEQ ID NO 21
<211> LENGTH: 19
<212> TYPE: PRT
<213> ORGANISM: Homo sapiens

<400> SEQUENCE: 21

Ser Ser Leu Leu Glu Lys Gly Leu Asp Gly Ala Lys Lys Ala Val Gly
1               5                   10                  15

Gly Leu Gly

<210> SEQ ID NO 22
<211> LENGTH: 18
<212> TYPE: PRT
<213> ORGANISM: Homo sapiens

<400> SEQUENCE: 22

Ser Ser Leu Leu Glu Lys Gly Leu Asp Gly Ala Lys Lys Ala Val Gly
1               5                   10                  15

Gly Leu

<210> SEQ ID NO 23
<211> LENGTH: 17
<212> TYPE: PRT
<213> ORGANISM: Homo sapiens

<400> SEQUENCE: 23

Ser Ser Leu Leu Glu Lys Gly Leu Asp Gly Ala Lys Lys Ala Val Gly
1               5                   10                  15

Gly

<210> SEQ ID NO 24
<211> LENGTH: 16
<212> TYPE: PRT
<213> ORGANISM: Homo sapiens

<400> SEQUENCE: 24

Ser Ser Leu Leu Glu Lys Gly Leu Asp Gly Ala Lys Lys Ala Val Gly
1               5                   10                  15

<210> SEQ ID NO 25
<211> LENGTH: 15
<212> TYPE: PRT
<213> ORGANISM: Homo sapiens

<400> SEQUENCE: 25

Ser Ser Leu Leu Glu Lys Gly Leu Asp Gly Ala Lys Lys Ala Val
1               5                   10                  15

<210> SEQ ID NO 26
<211> LENGTH: 14
<212> TYPE: PRT
<213> ORGANISM: Homo sapiens

<400> SEQUENCE: 26

Ser Ser Leu Leu Glu Lys Gly Leu Asp Gly Ala Lys Lys Ala
1               5                   10

<210> SEQ ID NO 27
<211> LENGTH: 13
<212> TYPE: PRT
<213> ORGANISM: Homo sapiens

<400> SEQUENCE: 27
```

```
Ser Ser Leu Leu Glu Lys Gly Leu Asp Gly Ala Lys Lys
1               5                   10

<210> SEQ ID NO 28
<211> LENGTH: 12
<212> TYPE: PRT
<213> ORGANISM: Homo sapiens

<400> SEQUENCE: 28

Ser Ser Leu Leu Glu Lys Gly Leu Asp Gly Ala Lys
1               5                   10

<210> SEQ ID NO 29
<211> LENGTH: 11
<212> TYPE: PRT
<213> ORGANISM: Homo sapiens

<400> SEQUENCE: 29

Ser Ser Leu Leu Glu Lys Gly Leu Asp Gly Ala
1               5                   10

<210> SEQ ID NO 30
<211> LENGTH: 10
<212> TYPE: PRT
<213> ORGANISM: Homo sapiens

<400> SEQUENCE: 30

Ser Ser Leu Leu Glu Lys Gly Leu Asp Gly
1               5                   10

<210> SEQ ID NO 31
<211> LENGTH: 9
<212> TYPE: PRT
<213> ORGANISM: Homo sapiens

<400> SEQUENCE: 31

Ser Ser Leu Leu Glu Lys Gly Leu Asp
1               5

<210> SEQ ID NO 32
<211> LENGTH: 8
<212> TYPE: PRT
<213> ORGANISM: Homo sapiens

<400> SEQUENCE: 32

Ser Ser Leu Leu Glu Lys Gly Leu
1               5

<210> SEQ ID NO 33
<211> LENGTH: 7
<212> TYPE: PRT
<213> ORGANISM: Homo sapiens

<400> SEQUENCE: 33

Ser Ser Leu Leu Glu Lys Gly
1               5

<210> SEQ ID NO 34
<211> LENGTH: 6
<212> TYPE: PRT
<213> ORGANISM: Homo sapiens

<400> SEQUENCE: 34

Ser Ser Leu Leu Glu Lys
1               5
```

<210> SEQ ID NO 35
<211> LENGTH: 5
<212> TYPE: PRT
<213> ORGANISM: Homo sapiens

<400> SEQUENCE: 35

Ser Ser Leu Leu Glu
1               5

<210> SEQ ID NO 36
<211> LENGTH: 26
<212> TYPE: PRT
<213> ORGANISM: Homo sapiens

<400> SEQUENCE: 36

Ser Ser Leu Leu Glu Lys Gly Leu Asp Gly Ala Lys Lys Ala Val Gly
1               5                   10                  15

Gly Leu Gly Lys Leu Gly Lys Asp Ala Val
            20                  25

<210> SEQ ID NO 37
<211> LENGTH: 27
<212> TYPE: PRT
<213> ORGANISM: Homo sapiens

<400> SEQUENCE: 37

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu
            20                  25

<210> SEQ ID NO 38
<211> LENGTH: 28
<212> TYPE: PRT
<213> ORGANISM: Homo sapiens

<400> SEQUENCE: 38

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp
            20                  25

<210> SEQ ID NO 39
<211> LENGTH: 29
<212> TYPE: PRT
<213> ORGANISM: Homo sapiens

<400> SEQUENCE: 39

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu
            20                  25

<210> SEQ ID NO 40
<211> LENGTH: 30
<212> TYPE: PRT
<213> ORGANISM: Homo sapiens

<400> SEQUENCE: 40

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu
            20                  25                  30

```
<210> SEQ ID NO 41
<211> LENGTH: 31
<212> TYPE: PRT
<213> ORGANISM: Homo sapiens

<400> SEQUENCE: 41

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser
            20                  25                  30

<210> SEQ ID NO 42
<211> LENGTH: 32
<212> TYPE: PRT
<213> ORGANISM: Homo sapiens

<400> SEQUENCE: 42

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

<210> SEQ ID NO 43
<211> LENGTH: 33
<212> TYPE: PRT
<213> ORGANISM: Homo sapiens

<400> SEQUENCE: 43

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly

<210> SEQ ID NO 44
<211> LENGTH: 34
<212> TYPE: PRT
<213> ORGANISM: Homo sapiens

<400> SEQUENCE: 44

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys

<210> SEQ ID NO 45
<211> LENGTH: 35
<212> TYPE: PRT
<213> ORGANISM: Homo sapiens

<400> SEQUENCE: 45

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly
        35

<210> SEQ ID NO 46
```

```
<211> LENGTH: 36
<212> TYPE: PRT
<213> ORGANISM: Homo sapiens

<400> SEQUENCE: 46

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala
        35

<210> SEQ ID NO 47
<211> LENGTH: 37
<212> TYPE: PRT
<213> ORGANISM: Homo sapiens

<400> SEQUENCE: 47

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val
        35

<210> SEQ ID NO 48
<211> LENGTH: 38
<212> TYPE: PRT
<213> ORGANISM: Homo sapiens

<400> SEQUENCE: 48

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His
        35

<210> SEQ ID NO 49
<211> LENGTH: 39
<212> TYPE: PRT
<213> ORGANISM: Homo sapiens

<400> SEQUENCE: 49

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp
        35

<210> SEQ ID NO 50
<211> LENGTH: 40
<212> TYPE: PRT
<213> ORGANISM: Homo sapiens

<400> SEQUENCE: 50

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30
```

```
Gly Lys Gly Ala Val His Asp Val
        35                  40

<210> SEQ ID NO 51
<211> LENGTH: 41
<212> TYPE: PRT
<213> ORGANISM: Homo sapiens

<400> SEQUENCE: 51

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys
        35                  40

<210> SEQ ID NO 52
<211> LENGTH: 42
<212> TYPE: PRT
<213> ORGANISM: Homo sapiens

<400> SEQUENCE: 52

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys Asp
        35                  40

<210> SEQ ID NO 53
<211> LENGTH: 43
<212> TYPE: PRT
<213> ORGANISM: Homo sapiens

<400> SEQUENCE: 53

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys Asp Val
        35                  40

<210> SEQ ID NO 54
<211> LENGTH: 44
<212> TYPE: PRT
<213> ORGANISM: Homo sapiens

<400> SEQUENCE: 54

Ser Ser Leu Leu Glu Lys Gly Leu Asp Gly Ala Lys Lys Ala Val Gly
 1               5                  10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu
        35                  40

<210> SEQ ID NO 55
<211> LENGTH: 45
<212> TYPE: PRT
<213> ORGANISM: Homo sapiens

<400> SEQUENCE: 55

Ser Ser Leu Leu Glu Lys Gly Leu Asp Gly Ala Lys Lys Ala Val Gly
```

```
                1               5                  10                 15
Gly Leu Gly Lys Leu Gly Lys Asp Ala Val Glu Asp Leu Glu Ser Val
        20                  25                 30
Gly Lys Gly Ala Val His Asp Val Lys Asp Val Leu Asp
        35                  40                 45

<210> SEQ ID NO 56
<211> LENGTH: 46
<212> TYPE: PRT
<213> ORGANISM: Homo sapiens

<400> SEQUENCE: 56

Ser Ser Leu Leu Glu Lys Gly Leu Asp Gly Ala Lys Lys Ala Val Gly
1               5                  10                 15
Gly Leu Gly Lys Leu Gly Lys Asp Ala Val Glu Asp Leu Glu Ser Val
        20                  25                 30
Gly Lys Gly Ala Val His Asp Val Lys Asp Val Leu Asp Ser
        35                  40                 45

<210> SEQ ID NO 57
<211> LENGTH: 47
<212> TYPE: PRT
<213> ORGANISM: Homo sapiens

<400> SEQUENCE: 57

Ser Leu Leu Glu Lys Gly Leu Asp Gly Ala Lys Lys Ala Val Gly Gly
1               5                  10                 15
Leu Gly Lys Leu Gly Lys Asp Ala Val Glu Asp Leu Glu Ser Val Gly
        20                  25                 30
Lys Gly Ala Val His Asp Val Lys Asp Val Leu Asp Ser Val Leu
        35                  40                 45

<210> SEQ ID NO 58
<211> LENGTH: 46
<212> TYPE: PRT
<213> ORGANISM: Homo sapiens

<400> SEQUENCE: 58

Leu Leu Glu Lys Gly Leu Asp Gly Ala Lys Lys Ala Val Gly Gly Leu
1               5                  10                 15
Gly Lys Leu Gly Lys Asp Ala Val Glu Asp Leu Glu Ser Val Gly Lys
        20                  25                 30
Gly Ala Val His Asp Val Lys Asp Val Leu Asp Ser Val Leu
        35                  40                 45

<210> SEQ ID NO 59
<211> LENGTH: 45
<212> TYPE: PRT
<213> ORGANISM: Homo sapiens

<400> SEQUENCE: 59

Leu Glu Lys Gly Leu Asp Gly Ala Lys Lys Ala Val Gly Gly Leu Gly
1               5                  10                 15
Lys Leu Gly Lys Asp Ala Val Glu Asp Leu Glu Ser Val Gly Lys Gly
        20                  25                 30
Ala Val His Asp Val Lys Asp Val Leu Asp Ser Val Leu
        35                  40                 45

<210> SEQ ID NO 60
<211> LENGTH: 44
<212> TYPE: PRT
```

-continued

<213> ORGANISM: Homo sapiens

<400> SEQUENCE: 60

Glu Lys Gly Leu Asp Gly Ala Lys Lys Ala Val Gly Gly Leu Gly Lys
1               5                   10                  15

Leu Gly Lys Asp Ala Val Glu Asp Leu Glu Ser Val Gly Lys Gly Ala
            20                  25                  30

Val His Asp Val Lys Asp Val Leu Asp Ser Val Leu
        35                  40

<210> SEQ ID NO 61
<211> LENGTH: 43
<212> TYPE: PRT
<213> ORGANISM: Homo sapiens

<400> SEQUENCE: 61

Lys Gly Leu Asp Gly Ala Lys Lys Ala Val Gly Gly Leu Gly Lys Leu
1               5                   10                  15

Gly Lys Asp Ala Val Glu Asp Leu Glu Ser Val Gly Lys Gly Ala Val
            20                  25                  30

His Asp Val Lys Asp Val Leu Asp Ser Val Leu
        35                  40

<210> SEQ ID NO 62
<211> LENGTH: 42
<212> TYPE: PRT
<213> ORGANISM: Homo sapiens

<400> SEQUENCE: 62

Gly Leu Asp Gly Ala Lys Lys Ala Val Gly Gly Leu Gly Lys Leu Gly
1               5                   10                  15

Lys Asp Ala Val Glu Asp Leu Glu Ser Val Gly Lys Gly Ala Val His
            20                  25                  30

Asp Val Lys Asp Val Leu Asp Ser Val Leu
        35                  40

<210> SEQ ID NO 63
<211> LENGTH: 41
<212> TYPE: PRT
<213> ORGANISM: Homo sapiens

<400> SEQUENCE: 63

Leu Asp Gly Ala Lys Lys Ala Val Gly Gly Leu Gly Lys Leu Gly Lys
1               5                   10                  15

Asp Ala Val Glu Asp Leu Glu Ser Val Gly Lys Gly Ala Val His Asp
            20                  25                  30

Val Lys Asp Val Leu Asp Ser Val Leu
        35                  40

<210> SEQ ID NO 64
<211> LENGTH: 40
<212> TYPE: PRT
<213> ORGANISM: Homo sapiens

<400> SEQUENCE: 64

Asp Gly Ala Lys Lys Ala Val Gly Gly Leu Gly Lys Leu Gly Lys Asp
1               5                   10                  15

Ala Val Glu Asp Leu Glu Ser Val Gly Lys Gly Ala Val His Asp Val
            20                  25                  30

Lys Asp Val Leu Asp Ser Val Leu
        35                  40

<210> SEQ ID NO 65
<211> LENGTH: 39
<212> TYPE: PRT
<213> ORGANISM: Homo sapiens

<400> SEQUENCE: 65

Gly Ala Lys Lys Ala Val Gly Gly Leu Gly Lys Leu Gly Lys Asp Ala
1               5                   10                  15

Val Glu Asp Leu Glu Ser Val Gly Lys Gly Ala Val His Asp Val Lys
                20                  25                  30

Asp Val Leu Asp Ser Val Leu
                35

<210> SEQ ID NO 66
<211> LENGTH: 38
<212> TYPE: PRT
<213> ORGANISM: Homo sapiens

<400> SEQUENCE: 66

Ala Lys Lys Ala Val Gly Gly Leu Gly Lys Leu Gly Lys Asp Ala Val
1               5                   10                  15

Glu Asp Leu Glu Ser Val Gly Lys Gly Ala Val His Asp Val Lys Asp
                20                  25                  30

Val Leu Asp Ser Val Leu
                35

<210> SEQ ID NO 67
<211> LENGTH: 37
<212> TYPE: PRT
<213> ORGANISM: Homo sapiens

<400> SEQUENCE: 67

Lys Lys Ala Val Gly Gly Leu Gly Lys Leu Gly Lys Asp Ala Val Glu
1               5                   10                  15

Asp Leu Glu Ser Val Gly Lys Gly Ala Val His Asp Val Lys Asp Val
                20                  25                  30

Leu Asp Ser Val Leu
                35

<210> SEQ ID NO 68
<211> LENGTH: 36
<212> TYPE: PRT
<213> ORGANISM: Homo sapiens

<400> SEQUENCE: 68

Lys Ala Val Gly Gly Leu Gly Lys Leu Gly Lys Asp Ala Val Glu Asp
1               5                   10                  15

Leu Glu Ser Val Gly Lys Gly Ala Val His Asp Val Lys Asp Val Leu
                20                  25                  30

Asp Ser Val Leu
                35

<210> SEQ ID NO 69
<211> LENGTH: 35
<212> TYPE: PRT
<213> ORGANISM: Homo sapiens

<400> SEQUENCE: 69

Ala Val Gly Gly Leu Gly Lys Leu Gly Lys Asp Ala Val Glu Asp Leu
1               5                   10                  15

Glu Ser Val Gly Lys Gly Ala Val His Asp Val Lys Asp Val Leu Asp
            20                  25                  30

Ser Val Leu
         35

<210> SEQ ID NO 70
<211> LENGTH: 34
<212> TYPE: PRT
<213> ORGANISM: Homo sapiens

<400> SEQUENCE: 70

Val Gly Gly Leu Gly Lys Leu Gly Lys Asp Ala Val Glu Asp Leu Glu
 1               5                  10                  15

Ser Val Gly Lys Gly Ala Val His Asp Val Lys Asp Val Leu Asp Ser
            20                  25                  30

Val Leu

<210> SEQ ID NO 71
<211> LENGTH: 33
<212> TYPE: PRT
<213> ORGANISM: Homo sapiens

<400> SEQUENCE: 71

Gly Gly Leu Gly Lys Leu Gly Lys Asp Ala Val Glu Asp Leu Glu Ser
 1               5                  10                  15

Val Gly Lys Gly Ala Val His Asp Val Lys Asp Val Leu Asp Ser Val
            20                  25                  30

Leu

<210> SEQ ID NO 72
<211> LENGTH: 32
<212> TYPE: PRT
<213> ORGANISM: Homo sapiens

<400> SEQUENCE: 72

Gly Leu Gly Lys Leu Gly Lys Asp Ala Val Glu Asp Leu Glu Ser Val
 1               5                  10                  15

Gly Lys Gly Ala Val His Asp Val Lys Asp Val Leu Asp Ser Val Leu
            20                  25                  30

<210> SEQ ID NO 73
<211> LENGTH: 31
<212> TYPE: PRT
<213> ORGANISM: Homo sapiens

<400> SEQUENCE: 73

Leu Gly Lys Leu Gly Lys Asp Ala Val Glu Asp Leu Glu Ser Val Gly
 1               5                  10                  15

Lys Gly Ala Val His Asp Val Lys Asp Val Leu Asp Ser Val Leu
            20                  25                  30

<210> SEQ ID NO 74
<211> LENGTH: 30
<212> TYPE: PRT
<213> ORGANISM: Homo sapiens

<400> SEQUENCE: 74

Gly Lys Leu Gly Lys Asp Ala Val Glu Asp Leu Glu Ser Val Gly Lys
 1               5                  10                  15

Gly Ala Val His Asp Val Lys Asp Val Leu Asp Ser Val Leu
            20                  25                  30

```
<210> SEQ ID NO 75
<211> LENGTH: 29
<212> TYPE: PRT
<213> ORGANISM: Homo sapiens

<400> SEQUENCE: 75

Lys Leu Gly Lys Asp Ala Val Glu Asp Leu Glu Ser Val Gly Lys Gly
1               5                   10                  15

Ala Val His Asp Val Lys Asp Val Leu Asp Ser Val Leu
            20                  25

<210> SEQ ID NO 76
<211> LENGTH: 28
<212> TYPE: PRT
<213> ORGANISM: Homo sapiens

<400> SEQUENCE: 76

Leu Gly Lys Asp Ala Val Glu Asp Leu Glu Ser Val Gly Lys Gly Ala
1               5                   10                  15

Val His Asp Val Lys Asp Val Leu Asp Ser Val Leu
            20                  25

<210> SEQ ID NO 77
<211> LENGTH: 27
<212> TYPE: PRT
<213> ORGANISM: Homo sapiens

<400> SEQUENCE: 77

Gly Lys Asp Ala Val Glu Asp Leu Glu Ser Val Gly Lys Gly Ala Val
1               5                   10                  15

His Asp Val Lys Asp Val Leu Asp Ser Val Leu
            20                  25

<210> SEQ ID NO 78
<211> LENGTH: 26
<212> TYPE: PRT
<213> ORGANISM: Homo sapiens

<400> SEQUENCE: 78

Lys Asp Ala Val Glu Asp Leu Glu Ser Val Gly Lys Gly Ala Val His
1               5                   10                  15

Asp Val Lys Asp Val Leu Asp Ser Val Leu
            20                  25

<210> SEQ ID NO 79
<211> LENGTH: 25
<212> TYPE: PRT
<213> ORGANISM: Homo sapiens

<400> SEQUENCE: 79

Asp Ala Val Glu Asp Leu Glu Ser Val Gly Lys Gly Ala Val His Asp
1               5                   10                  15

Val Lys Asp Val Leu Asp Ser Val Leu
            20                  25

<210> SEQ ID NO 80
<211> LENGTH: 24
<212> TYPE: PRT
<213> ORGANISM: Homo sapiens

<400> SEQUENCE: 80

Ala Val Glu Asp Leu Glu Ser Val Gly Lys Gly Ala Val His Asp Val
1               5                   10                  15
```

Lys Asp Val Leu Asp Ser Val Leu
            20

<210> SEQ ID NO 81
<211> LENGTH: 23
<212> TYPE: PRT
<213> ORGANISM: Homo sapiens

<400> SEQUENCE: 81

Val Glu Asp Leu Glu Ser Val Gly Lys Gly Ala Val His Asp Val Lys
1               5                   10                  15

Asp Val Leu Asp Ser Val Leu
            20

<210> SEQ ID NO 82
<211> LENGTH: 22
<212> TYPE: PRT
<213> ORGANISM: Homo sapiens

<400> SEQUENCE: 82

Glu Asp Leu Glu Ser Val Gly Lys Gly Ala Val His Asp Val Lys Asp
1               5                   10                  15

Val Leu Asp Ser Val Leu
            20

<210> SEQ ID NO 83
<211> LENGTH: 21
<212> TYPE: PRT
<213> ORGANISM: Homo sapiens

<400> SEQUENCE: 83

Asp Leu Glu Ser Val Gly Lys Gly Ala Val His Asp Val Lys Asp Val
1               5                   10                  15

Leu Asp Ser Val Leu
            20

<210> SEQ ID NO 84
<211> LENGTH: 20
<212> TYPE: PRT
<213> ORGANISM: Homo sapiens

<400> SEQUENCE: 84

Leu Glu Ser Val Gly Lys Gly Ala Val His Asp Val Lys Asp Val Leu
1               5                   10                  15

Asp Ser Val Leu
            20

<210> SEQ ID NO 85
<211> LENGTH: 19
<212> TYPE: PRT
<213> ORGANISM: Homo sapiens

<400> SEQUENCE: 85

Glu Ser Val Gly Lys Gly Ala Val His Asp Val Lys Asp Val Leu Asp
1               5                   10                  15

Ser Val Leu

<210> SEQ ID NO 86
<211> LENGTH: 18
<212> TYPE: PRT
<213> ORGANISM: Homo sapiens

<400> SEQUENCE: 86

Ser Val Gly Lys Gly Ala Val His Asp Val Lys Asp Val Leu Asp Ser
1               5                   10                  15

Val Leu

<210> SEQ ID NO 87
<211> LENGTH: 17
<212> TYPE: PRT
<213> ORGANISM: Homo sapiens

<400> SEQUENCE: 87

Val Gly Lys Gly Ala Val His Asp Val Lys Asp Val Leu Asp Ser Val
1               5                   10                  15

Leu

<210> SEQ ID NO 88
<211> LENGTH: 16
<212> TYPE: PRT
<213> ORGANISM: Homo sapiens

<400> SEQUENCE: 88

Gly Lys Gly Ala Val His Asp Val Lys Asp Val Leu Asp Ser Val Leu
1               5                   10                  15

<210> SEQ ID NO 89
<211> LENGTH: 15
<212> TYPE: PRT
<213> ORGANISM: Homo sapiens

<400> SEQUENCE: 89

Lys Gly Ala Val His Asp Val Lys Asp Val Leu Asp Ser Val Leu
1               5                   10                  15

<210> SEQ ID NO 90
<211> LENGTH: 14
<212> TYPE: PRT
<213> ORGANISM: Homo sapiens

<400> SEQUENCE: 90

Gly Ala Val His Asp Val Lys Asp Val Leu Asp Ser Val Leu
1               5                   10

<210> SEQ ID NO 91
<211> LENGTH: 13
<212> TYPE: PRT
<213> ORGANISM: Homo sapiens

<400> SEQUENCE: 91

Ala Val His Asp Val Lys Asp Val Leu Asp Ser Val Leu
1               5                   10

<210> SEQ ID NO 92
<211> LENGTH: 12
<212> TYPE: PRT
<213> ORGANISM: Homo sapiens

<400> SEQUENCE: 92

Val His Asp Val Lys Asp Val Leu Asp Ser Val Leu
1               5                   10

<210> SEQ ID NO 93
<211> LENGTH: 11
<212> TYPE: PRT
<213> ORGANISM: Homo sapiens

```
<400> SEQUENCE: 93

His Asp Val Lys Asp Val Leu Asp Ser Val Leu
1               5                   10

<210> SEQ ID NO 94
<211> LENGTH: 10
<212> TYPE: PRT
<213> ORGANISM: Homo sapiens

<400> SEQUENCE: 94

Asp Val Lys Asp Val Leu Asp Ser Val Leu
1               5                   10

<210> SEQ ID NO 95
<211> LENGTH: 46
<212> TYPE: PRT
<213> ORGANISM: Homo sapiens

<400> SEQUENCE: 95

Ser Leu Leu Glu Lys Gly Leu Asp Gly Ala Lys Lys Ala Val Gly Gly
1               5                   10                  15

Leu Gly Lys Leu Gly Lys Asp Ala Val Glu Asp Leu Glu Ser Val Gly
            20                  25                  30

Lys Gly Ala Val His Asp Val Lys Asp Val Leu Asp Ser Val
        35                  40                  45

<210> SEQ ID NO 96
<211> LENGTH: 45
<212> TYPE: PRT
<213> ORGANISM: Homo sapiens

<400> SEQUENCE: 96

Leu Leu Glu Lys Gly Leu Asp Gly Ala Lys Lys Ala Val Gly Gly Leu
1               5                   10                  15

Gly Lys Leu Gly Lys Asp Ala Val Glu Asp Leu Glu Ser Val Gly Lys
            20                  25                  30

Gly Ala Val His Asp Val Lys Asp Val Leu Asp Ser Val
        35                  40                  45

<210> SEQ ID NO 97
<211> LENGTH: 44
<212> TYPE: PRT
<213> ORGANISM: Homo sapiens

<400> SEQUENCE: 97

Leu Glu Lys Gly Leu Asp Gly Ala Lys Lys Ala Val Gly Gly Leu Gly
1               5                   10                  15

Lys Leu Gly Lys Asp Ala Val Glu Asp Leu Glu Ser Val Gly Lys Gly
            20                  25                  30

Ala Val His Asp Val Lys Asp Val Leu Asp Ser Val
        35                  40

<210> SEQ ID NO 98
<211> LENGTH: 43
<212> TYPE: PRT
<213> ORGANISM: Homo sapiens

<400> SEQUENCE: 98

Glu Lys Gly Leu Asp Gly Ala Lys Lys Ala Val Gly Gly Leu Gly Lys
1               5                   10                  15

Leu Gly Lys Asp Ala Val Glu Asp Leu Glu Ser Val Gly Lys Gly Ala
            20                  25                  30
```

Val His Asp Val Lys Asp Val Leu Asp Ser Val
            35                  40

<210> SEQ ID NO 99
<211> LENGTH: 42
<212> TYPE: PRT
<213> ORGANISM: Homo sapiens

<400> SEQUENCE: 99

Lys Gly Leu Asp Gly Ala Lys Lys Ala Val Gly Gly Leu Gly Lys Leu
 1               5                  10                  15

Gly Lys Asp Ala Val Glu Asp Leu Glu Ser Val Gly Lys Gly Ala Val
            20                  25                  30

His Asp Val Lys Asp Val Leu Asp Ser Val
            35                  40

<210> SEQ ID NO 100
<211> LENGTH: 41
<212> TYPE: PRT
<213> ORGANISM: Homo sapiens

<400> SEQUENCE: 100

Gly Leu Asp Gly Ala Lys Lys Ala Val Gly Gly Leu Gly Lys Leu Gly
 1               5                  10                  15

Lys Asp Ala Val Glu Asp Leu Glu Ser Val Gly Lys Gly Ala Val His
            20                  25                  30

Asp Val Lys Asp Val Leu Asp Ser Val
            35                  40

<210> SEQ ID NO 101
<211> LENGTH: 40
<212> TYPE: PRT
<213> ORGANISM: Homo sapiens

<400> SEQUENCE: 101

Leu Asp Gly Ala Lys Lys Ala Val Gly Gly Leu Gly Lys Leu Gly Lys
 1               5                  10                  15

Asp Ala Val Glu Asp Leu Glu Ser Val Gly Lys Gly Ala Val His Asp
            20                  25                  30

Val Lys Asp Val Leu Asp Ser Val
            35                  40

<210> SEQ ID NO 102
<211> LENGTH: 39
<212> TYPE: PRT
<213> ORGANISM: Homo sapiens

<400> SEQUENCE: 102

Asp Gly Ala Lys Lys Ala Val Gly Gly Leu Gly Lys Leu Gly Lys Asp
 1               5                  10                  15

Ala Val Glu Asp Leu Glu Ser Val Gly Lys Gly Ala Val His Asp Val
            20                  25                  30

Lys Asp Val Leu Asp Ser Val
            35

<210> SEQ ID NO 103
<211> LENGTH: 38
<212> TYPE: PRT
<213> ORGANISM: Homo sapiens

<400> SEQUENCE: 103

```
Gly Ala Lys Lys Ala Val Gly Gly Leu Gly Lys Leu Gly Lys Asp Ala
 1               5                  10                  15

Val Glu Asp Leu Glu Ser Val Gly Lys Gly Ala Val His Asp Val Lys
            20                  25                  30

Asp Val Leu Asp Ser Val
            35
```

<210> SEQ ID NO 104
<211> LENGTH: 37
<212> TYPE: PRT
<213> ORGANISM: Homo sapiens

<400> SEQUENCE: 104

```
Ala Lys Lys Ala Val Gly Gly Leu Gly Lys Leu Gly Lys Asp Ala Val
 1               5                  10                  15

Glu Asp Leu Glu Ser Val Gly Lys Gly Ala Val His Asp Val Lys Asp
            20                  25                  30

Val Leu Asp Ser Val
            35
```

<210> SEQ ID NO 105
<211> LENGTH: 36
<212> TYPE: PRT
<213> ORGANISM: Homo sapiens

<400> SEQUENCE: 105

```
Lys Lys Ala Val Gly Gly Leu Gly Lys Leu Gly Lys Asp Ala Val Glu
 1               5                  10                  15

Asp Leu Glu Ser Val Gly Lys Gly Ala Val His Asp Val Lys Asp Val
            20                  25                  30

Leu Asp Ser Val
            35
```

<210> SEQ ID NO 106
<211> LENGTH: 35
<212> TYPE: PRT
<213> ORGANISM: Homo sapiens

<400> SEQUENCE: 106

```
Lys Ala Val Gly Gly Leu Gly Lys Leu Gly Lys Asp Ala Val Glu Asp
 1               5                  10                  15

Leu Glu Ser Val Gly Lys Gly Ala Val His Asp Val Lys Asp Val Leu
            20                  25                  30

Asp Ser Val
            35
```

<210> SEQ ID NO 107
<211> LENGTH: 34
<212> TYPE: PRT
<213> ORGANISM: Homo sapiens

<400> SEQUENCE: 107

```
Ala Val Gly Gly Leu Gly Lys Leu Gly Lys Asp Ala Val Glu Asp Leu
 1               5                  10                  15

Glu Ser Val Gly Lys Gly Ala Val His Asp Val Lys Asp Val Leu Asp
            20                  25                  30

Ser Val
```

<210> SEQ ID NO 108
<211> LENGTH: 33
<212> TYPE: PRT

<213> ORGANISM: Homo sapiens

<400> SEQUENCE: 108

Val Gly Gly Leu Gly Lys Leu Gly Lys Asp Ala Val Glu Asp Leu Glu
1               5                   10                  15

Ser Val Gly Lys Gly Ala Val His Asp Val Lys Asp Val Leu Asp Ser
            20                  25                  30

Val

<210> SEQ ID NO 109
<211> LENGTH: 32
<212> TYPE: PRT
<213> ORGANISM: Homo sapiens

<400> SEQUENCE: 109

Gly Gly Leu Gly Lys Leu Gly Lys Asp Ala Val Glu Asp Leu Glu Ser
1               5                   10                  15

Val Gly Lys Gly Ala Val His Asp Val Lys Asp Val Leu Asp Ser Val
            20                  25                  30

<210> SEQ ID NO 110
<211> LENGTH: 31
<212> TYPE: PRT
<213> ORGANISM: Homo sapiens

<400> SEQUENCE: 110

Gly Leu Gly Lys Leu Gly Lys Asp Ala Val Glu Asp Leu Glu Ser Val
1               5                   10                  15

Gly Lys Gly Ala Val His Asp Val Lys Asp Val Leu Asp Ser Val
            20                  25                  30

<210> SEQ ID NO 111
<211> LENGTH: 30
<212> TYPE: PRT
<213> ORGANISM: Homo sapiens

<400> SEQUENCE: 111

Leu Gly Lys Leu Gly Lys Asp Ala Val Glu Asp Leu Glu Ser Val Gly
1               5                   10                  15

Lys Gly Ala Val His Asp Val Lys Asp Val Leu Asp Ser Val
            20                  25                  30

<210> SEQ ID NO 112
<211> LENGTH: 29
<212> TYPE: PRT
<213> ORGANISM: Homo sapiens

<400> SEQUENCE: 112

Gly Lys Leu Gly Lys Asp Ala Val Glu Asp Leu Glu Ser Val Gly Lys
1               5                   10                  15

Gly Ala Val His Asp Val Lys Asp Val Leu Asp Ser Val
            20                  25

<210> SEQ ID NO 113
<211> LENGTH: 28
<212> TYPE: PRT
<213> ORGANISM: Homo sapiens

<400> SEQUENCE: 113

Lys Leu Gly Lys Asp Ala Val Glu Asp Leu Glu Ser Val Gly Lys Gly
1               5                   10                  15

Ala Val His Asp Val Lys Asp Val Leu Asp Ser Val

-continued

<210> SEQ ID NO 114
<211> LENGTH: 27
<212> TYPE: PRT
<213> ORGANISM: Homo sapiens

<400> SEQUENCE: 114

Leu Gly Lys Asp Ala Val Glu Asp Leu Glu Ser Val Gly Lys Gly Ala
 1               5                  10                  15

Val His Asp Val Lys Asp Val Leu Asp Ser Val
            20                  25

<210> SEQ ID NO 115
<211> LENGTH: 26
<212> TYPE: PRT
<213> ORGANISM: Homo sapiens

<400> SEQUENCE: 115

Gly Lys Asp Ala Val Glu Asp Leu Glu Ser Val Gly Lys Gly Ala Val
 1               5                  10                  15

His Asp Val Lys Asp Val Leu Asp Ser Val
            20                  25

<210> SEQ ID NO 116
<211> LENGTH: 25
<212> TYPE: PRT
<213> ORGANISM: Homo sapiens

<400> SEQUENCE: 116

Lys Asp Ala Val Glu Asp Leu Glu Ser Val Gly Lys Gly Ala Val His
 1               5                  10                  15

Asp Val Lys Asp Val Leu Asp Ser Val
            20                  25

<210> SEQ ID NO 117
<211> LENGTH: 24
<212> TYPE: PRT
<213> ORGANISM: Homo sapiens

<400> SEQUENCE: 117

Asp Ala Val Glu Asp Leu Glu Ser Val Gly Lys Gly Ala Val His Asp
 1               5                  10                  15

Val Lys Asp Val Leu Asp Ser Val
            20

<210> SEQ ID NO 118
<211> LENGTH: 23
<212> TYPE: PRT
<213> ORGANISM: Homo sapiens

<400> SEQUENCE: 118

Ala Val Glu Asp Leu Glu Ser Val Gly Lys Gly Ala Val His Asp Val
 1               5                  10                  15

Lys Asp Val Leu Asp Ser Val
            20

<210> SEQ ID NO 119
<211> LENGTH: 22
<212> TYPE: PRT
<213> ORGANISM: Homo sapiens

<400> SEQUENCE: 119

```
Val Glu Asp Leu Glu Ser Val Gly Lys Gly Ala Val His Asp Val Lys
 1               5                  10                  15

Asp Val Leu Asp Ser Val
            20
```

<210> SEQ ID NO 120
<211> LENGTH: 21
<212> TYPE: PRT
<213> ORGANISM: Homo sapiens

<400> SEQUENCE: 120

```
Glu Asp Leu Glu Ser Val Gly Lys Gly Ala Val His Asp Val Lys Asp
 1               5                  10                  15

Val Leu Asp Ser Val
            20
```

<210> SEQ ID NO 121
<211> LENGTH: 20
<212> TYPE: PRT
<213> ORGANISM: Homo sapiens

<400> SEQUENCE: 121

```
Asp Leu Glu Ser Val Gly Lys Gly Ala Val His Asp Val Lys Asp Val
 1               5                  10                  15

Leu Asp Ser Val
            20
```

<210> SEQ ID NO 122
<211> LENGTH: 19
<212> TYPE: PRT
<213> ORGANISM: Homo sapiens

<400> SEQUENCE: 122

```
Leu Glu Ser Val Gly Lys Gly Ala Val His Asp Val Lys Asp Val Leu
 1               5                  10                  15

Asp Ser Val
```

<210> SEQ ID NO 123
<211> LENGTH: 18
<212> TYPE: PRT
<213> ORGANISM: Homo sapiens

<400> SEQUENCE: 123

```
Glu Ser Val Gly Lys Gly Ala Val His Asp Val Lys Asp Val Leu Asp
 1               5                  10                  15

Ser Val
```

<210> SEQ ID NO 124
<211> LENGTH: 17
<212> TYPE: PRT
<213> ORGANISM: Homo sapiens

<400> SEQUENCE: 124

```
Ser Val Gly Lys Gly Ala Val His Asp Val Lys Asp Val Leu Asp Ser
 1               5                  10                  15

Val
```

<210> SEQ ID NO 125
<211> LENGTH: 16
<212> TYPE: PRT
<213> ORGANISM: Homo sapiens

<400> SEQUENCE: 125

```
Val Gly Lys Gly Ala Val His Asp Val Lys Asp Val Leu Asp Ser Val
 1               5                  10                  15
```

<210> SEQ ID NO 126
<211> LENGTH: 15
<212> TYPE: PRT
<213> ORGANISM: Homo sapiens

<400> SEQUENCE: 126

```
Gly Lys Gly Ala Val His Asp Val Lys Asp Val Leu Asp Ser Val
 1               5                  10                  15
```

<210> SEQ ID NO 127
<211> LENGTH: 14
<212> TYPE: PRT
<213> ORGANISM: Homo sapiens

<400> SEQUENCE: 127

```
Lys Gly Ala Val His Asp Val Lys Asp Val Leu Asp Ser Val
 1               5                  10
```

<210> SEQ ID NO 128
<211> LENGTH: 13
<212> TYPE: PRT
<213> ORGANISM: Homo sapiens

<400> SEQUENCE: 128

```
Gly Ala Val His Asp Val Lys Asp Val Leu Asp Ser Val
 1               5                  10
```

<210> SEQ ID NO 129
<211> LENGTH: 12
<212> TYPE: PRT
<213> ORGANISM: Homo sapiens

<400> SEQUENCE: 129

```
Ala Val His Asp Val Lys Asp Val Leu Asp Ser Val
 1               5                  10
```

<210> SEQ ID NO 130
<211> LENGTH: 11
<212> TYPE: PRT
<213> ORGANISM: Homo sapiens

<400> SEQUENCE: 130

```
Val His Asp Val Lys Asp Val Leu Asp Ser Val
 1               5                  10
```

<210> SEQ ID NO 131
<211> LENGTH: 10
<212> TYPE: PRT
<213> ORGANISM: Homo sapiens

<400> SEQUENCE: 131

```
His Asp Val Lys Asp Val Leu Asp Ser Val
 1               5                  10
```

<210> SEQ ID NO 132
<211> LENGTH: 22
<212> TYPE: PRT
<213> ORGANISM: Homo sapiens

<400> SEQUENCE: 132

```
Ser Leu Leu Glu Lys Gly Leu Asp Gly Ala Lys Lys Ala Val Gly Gly
 1               5                  10                  15
```

```
Leu Gly Lys Leu Gly Lys
            20

<210> SEQ ID NO 133
<211> LENGTH: 21
<212> TYPE: PRT
<213> ORGANISM: Homo sapiens

<400> SEQUENCE: 133

Leu Leu Glu Lys Gly Leu Asp Gly Ala Lys Lys Ala Val Gly Gly Leu
1               5                   10                  15

Gly Lys Leu Gly Lys
            20

<210> SEQ ID NO 134
<211> LENGTH: 20
<212> TYPE: PRT
<213> ORGANISM: Homo sapiens

<400> SEQUENCE: 134

Leu Glu Lys Gly Leu Asp Gly Ala Lys Lys Ala Val Gly Gly Leu Gly
1               5                   10                  15

Lys Leu Gly Lys
            20

<210> SEQ ID NO 135
<211> LENGTH: 19
<212> TYPE: PRT
<213> ORGANISM: Homo sapiens

<400> SEQUENCE: 135

Glu Lys Gly Leu Asp Gly Ala Lys Lys Ala Val Gly Gly Leu Gly Lys
1               5                   10                  15

Leu Gly Lys

<210> SEQ ID NO 136
<211> LENGTH: 18
<212> TYPE: PRT
<213> ORGANISM: Homo sapiens

<400> SEQUENCE: 136

Lys Gly Leu Asp Gly Ala Lys Lys Ala Val Gly Gly Leu Gly Lys Leu
1               5                   10                  15

Gly Lys

<210> SEQ ID NO 137
<211> LENGTH: 17
<212> TYPE: PRT
<213> ORGANISM: Homo sapiens

<400> SEQUENCE: 137

Gly Leu Asp Gly Ala Lys Lys Ala Val Gly Gly Leu Gly Lys Leu Gly
1               5                   10                  15

Lys

<210> SEQ ID NO 138
<211> LENGTH: 16
<212> TYPE: PRT
<213> ORGANISM: Homo sapiens

<400> SEQUENCE: 138

Leu Asp Gly Ala Lys Lys Ala Val Gly Gly Leu Gly Lys Leu Gly Lys
```

```
                1               5                  10                  15
```

<210> SEQ ID NO 139
<211> LENGTH: 15
<212> TYPE: PRT
<213> ORGANISM: Homo sapiens

<400> SEQUENCE: 139

```
Asp Gly Ala Lys Lys Ala Val Gly Gly Leu Gly Lys Leu Gly Lys
  1               5                  10                  15
```

<210> SEQ ID NO 140
<211> LENGTH: 14
<212> TYPE: PRT
<213> ORGANISM: Homo sapiens

<400> SEQUENCE: 140

```
Gly Ala Lys Lys Ala Val Gly Gly Leu Gly Lys Leu Gly Lys
  1               5                  10
```

<210> SEQ ID NO 141
<211> LENGTH: 13
<212> TYPE: PRT
<213> ORGANISM: Homo sapiens

<400> SEQUENCE: 141

```
Ala Lys Lys Ala Val Gly Gly Leu Gly Lys Leu Gly Lys
  1               5                  10
```

<210> SEQ ID NO 142
<211> LENGTH: 12
<212> TYPE: PRT
<213> ORGANISM: Homo sapiens

<400> SEQUENCE: 142

```
Lys Lys Ala Val Gly Gly Leu Gly Lys Leu Gly Lys
  1               5                  10
```

<210> SEQ ID NO 143
<211> LENGTH: 11
<212> TYPE: PRT
<213> ORGANISM: Homo sapiens

<400> SEQUENCE: 143

```
Lys Ala Val Gly Gly Leu Gly Lys Leu Gly Lys
  1               5                  10
```

<210> SEQ ID NO 144
<211> LENGTH: 10
<212> TYPE: PRT
<213> ORGANISM: Homo sapiens

<400> SEQUENCE: 144

```
Ala Val Gly Gly Leu Gly Lys Leu Gly Lys
  1               5                  10
```

<210> SEQ ID NO 145
<211> LENGTH: 25
<212> TYPE: PRT
<213> ORGANISM: Homo sapiens

<400> SEQUENCE: 145

```
Ser Ser Leu Leu Glu Lys Gly Leu Asp Gly Ala Lys Lys Ala Val Gly
  1               5                  10                  15

Gly Leu Gly Lys Leu Gly Lys Asp Ala
```

-continued

<210> SEQ ID NO 146
<211> LENGTH: 24
<212> TYPE: PRT
<213> ORGANISM: Homo sapiens

<400> SEQUENCE: 146

Ser Leu Leu Glu Lys Gly Leu Asp Gly Ala Lys Lys Ala Val Gly Gly
 1               5                  10                  15

Leu Gly Lys Leu Gly Lys Asp Ala
            20

<210> SEQ ID NO 147
<211> LENGTH: 23
<212> TYPE: PRT
<213> ORGANISM: Homo sapiens

<400> SEQUENCE: 147

Leu Leu Glu Lys Gly Leu Asp Gly Ala Lys Lys Ala Val Gly Gly Leu
 1               5                  10                  15

Gly Lys Leu Gly Lys Asp Ala
            20

<210> SEQ ID NO 148
<211> LENGTH: 22
<212> TYPE: PRT
<213> ORGANISM: Homo sapiens

<400> SEQUENCE: 148

Leu Glu Lys Gly Leu Asp Gly Ala Lys Lys Ala Val Gly Gly Leu Gly
 1               5                  10                  15

Lys Leu Gly Lys Asp Ala
            20

<210> SEQ ID NO 149
<211> LENGTH: 21
<212> TYPE: PRT
<213> ORGANISM: Homo sapiens

<400> SEQUENCE: 149

Glu Lys Gly Leu Asp Gly Ala Lys Lys Ala Val Gly Gly Leu Gly Lys
 1               5                  10                  15

Leu Gly Lys Asp Ala
            20

<210> SEQ ID NO 150
<211> LENGTH: 20
<212> TYPE: PRT
<213> ORGANISM: Homo sapiens

<400> SEQUENCE: 150

Lys Gly Leu Asp Gly Ala Lys Lys Ala Val Gly Gly Leu Gly Lys Leu
 1               5                  10                  15

Gly Lys Asp Ala
            20

<210> SEQ ID NO 151
<211> LENGTH: 19
<212> TYPE: PRT
<213> ORGANISM: Homo sapiens

<400> SEQUENCE: 151

```
Gly Leu Asp Gly Ala Lys Lys Ala Val Gly Gly Leu Gly Lys Leu Gly
1               5                   10                  15

Lys Asp Ala

<210> SEQ ID NO 152
<211> LENGTH: 18
<212> TYPE: PRT
<213> ORGANISM: Homo sapiens

<400> SEQUENCE: 152

Leu Asp Gly Ala Lys Lys Ala Val Gly Gly Leu Gly Lys Leu Gly Lys
1               5                   10                  15

Asp Ala

<210> SEQ ID NO 153
<211> LENGTH: 17
<212> TYPE: PRT
<213> ORGANISM: Homo sapiens

<400> SEQUENCE: 153

Asp Gly Ala Lys Lys Ala Val Gly Gly Leu Gly Lys Leu Gly Lys Asp
1               5                   10                  15

Ala

<210> SEQ ID NO 154
<211> LENGTH: 16
<212> TYPE: PRT
<213> ORGANISM: Homo sapiens

<400> SEQUENCE: 154

Gly Ala Lys Lys Ala Val Gly Gly Leu Gly Lys Leu Gly Lys Asp Ala
1               5                   10                  15

<210> SEQ ID NO 155
<211> LENGTH: 15
<212> TYPE: PRT
<213> ORGANISM: Homo sapiens

<400> SEQUENCE: 155

Ala Lys Lys Ala Val Gly Gly Leu Gly Lys Leu Gly Lys Asp Ala
1               5                   10                  15

<210> SEQ ID NO 156
<211> LENGTH: 14
<212> TYPE: PRT
<213> ORGANISM: Homo sapiens

<400> SEQUENCE: 156

Lys Lys Ala Val Gly Gly Leu Gly Lys Leu Gly Lys Asp Ala
1               5                   10

<210> SEQ ID NO 157
<211> LENGTH: 13
<212> TYPE: PRT
<213> ORGANISM: Homo sapiens

<400> SEQUENCE: 157

Lys Ala Val Gly Gly Leu Gly Lys Leu Gly Lys Asp Ala
1               5                   10

<210> SEQ ID NO 158
<211> LENGTH: 12
<212> TYPE: PRT
<213> ORGANISM: Homo sapiens
```

```
<400> SEQUENCE: 158

Ala Val Gly Gly Leu Gly Lys Leu Gly Lys Asp Ala
 1               5                  10

<210> SEQ ID NO 159
<211> LENGTH: 11
<212> TYPE: PRT
<213> ORGANISM: Homo sapiens

<400> SEQUENCE: 159

Val Gly Gly Leu Gly Lys Leu Gly Lys Asp Ala
 1               5                  10

<210> SEQ ID NO 160
<211> LENGTH: 10
<212> TYPE: PRT
<213> ORGANISM: Homo sapiens

<400> SEQUENCE: 160

Gly Gly Leu Gly Lys Leu Gly Lys Asp Ala
 1               5                  10

<210> SEQ ID NO 161
<211> LENGTH: 24
<212> TYPE: PRT
<213> ORGANISM: Homo sapiens

<400> SEQUENCE: 161

Ser Ser Leu Leu Glu Lys Gly Leu Asp Gly Ala Lys Lys Ala Val Gly
 1               5                  10                  15

Gly Leu Gly Lys Leu Gly Lys Asp
                20
```